US006891369B2

(12) United States Patent
Hurlimann et al.

(10) Patent No.: US 6,891,369 B2
(45) Date of Patent: May 10, 2005

(54) NUCLEAR MAGNETIC RESONANCE METHOD AND LOGGING APPARATUS FOR FLUID ANALYSIS

(75) Inventors: Martin D. Hurlimann, Ridgefield, CT (US); Charles Flaum, Ridgefield, CT (US); Mark Flaum, Houston, TX (US); Lalitha Venkataramanan, Stamford, CT (US); Robert L. Kleinberg, Ridgefield, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 10/318,798

(22) Filed: Dec. 13, 2002

(65) Prior Publication Data

US 2003/0178994 A1 Sep. 25, 2003

Related U.S. Application Data

(63) Continuation-in-part of application No. 10/016,246, filed on Oct. 30, 2001.

(51) Int. Cl.[7] ............................................. G01V 3/00
(52) U.S. Cl. ........................................................ 324/303
(58) Field of Search ............................... 324/300, 303, 324/306–309

(56) References Cited

U.S. PATENT DOCUMENTS

| | | | |
|---|---|---|---|
| 4,860,581 A | 8/1989 | Zimmerman et al. | 73/155 |
| 4,936,139 A | 6/1990 | Zimmerman et al. | 73/155 |
| 5,023,551 A | 6/1991 | Kleinberg et al. | 324/303 |
| 5,306,640 A | 4/1994 | Vinegar et al. | 436/29 |
| 5,680,043 A | * 10/1997 | Hurlimann et al. | 324/303 |
| 5,696,448 A | * 12/1997 | Coates et al. | 324/303 |
| 5,796,252 A | 8/1998 | Kleinberg et al. | 324/303 |
| 5,939,717 A | 8/1999 | Mullins | 250/255 |
| 6,107,796 A | 8/2000 | Prammer | 324/303 |
| 6,111,408 A | 8/2000 | Blades et al. | 324/303 |
| 6,111,409 A | 8/2000 | Edwards et al. | 324/303 |
| 6,184,681 B1 | * 2/2001 | Heidler et al. | 324/303 |
| 6,204,663 B1 | * 3/2001 | Prammer | 324/303 |
| 6,237,404 B1 | * 5/2001 | Crary et al. | 73/152.03 |
| 6,274,865 B1 | 8/2001 | Schroer et al. | 250/269.1 |
| 6,462,542 B1 | 10/2002 | Venkataramanan et al. | 324/303 |
| 6,492,809 B1 | * 12/2002 | Speier et al. | 324/303 |
| 6,522,136 B1 | * 2/2003 | Hurlimann et al. | 324/303 |

(Continued)

FOREIGN PATENT DOCUMENTS

GB 2 394 778 5/2004 ............ G01V/3/32

OTHER PUBLICATIONS

J. W. Amyx et al. Petroleum Reservoir Engineering. *McGraw-Hill* (1960), p. 458.

(Continued)

*Primary Examiner*—Christopher W. Fulton
*Assistant Examiner*—Dixomara Vargas
(74) *Attorney, Agent, or Firm*—Jody Lynn DeStefanis; William B. Batzer; John J. Ryberg

(57) ABSTRACT

The present invention discloses a diffusion edited pulse technique that allows information about a fluid to be extracted, comprising: a) obtaining a fluid sample; b) generating a sequence of magnetic field pulses in the fluid, the sequence comprising an initial magnetic field pulse, a first portion that follows the initial magnetic field pulse, and a second portion that follows the first portion; c) detecting magnetic resonance signals using the second portion of the sequence; d) modifying the first portion of the sequence, and repeating steps (b) and (c); and e) extracting information about the fluid by determining relaxation and diffusion characteristics and their correlation based on the signals detected in steps (c) and (d). Also disclosed is a logging tool equipped with a processor to implement the diffusion edited pulse technique.

64 Claims, 16 Drawing Sheets

U.S. PATENT DOCUMENTS

| | | | |
|---|---|---|---|
| 6,545,471 B1 * | 4/2003 | Wollin | 324/303 |
| 6,570,382 B1 * | 5/2003 | Hurlimann et al. | 324/303 |
| 6,646,438 B1 * | 11/2003 | Kruspe et al. | 324/303 |
| 2002/0067164 A1 | 6/2002 | Venkataramanan et al. | 324/307 |
| 2002/0140425 A1 | 10/2002 | Prammer et al. | |

OTHER PUBLICATIONS

E. R. Andrew. Nuclear Magnetic Resonance. *Cambridge Univ. Press* (1955), p. 127.

R. Badry et al. "Downhole Optical Analysis of Formation Fluids". *Oilfield Review* (Jan. 1994), pp. 21–28.

Bloembergen et al. "Relaxation Effects in Nuclear Magnetic Resonance Absorption". *Physical Review* (1948), vol. 73, No. 7, pp. 679–712.

R. E. Botto, "Fossil Fuels". *Encyclopedia of Nuclear Mag. Resonance* (1996), pp. 1–17.

CRC Handbook of Chemistry and Physics (63rd Edition). *CRC Press* (1982–1983), pp. B–73–B–165.

P. T. Callaghan. Principles of Nuclear Magnetic Resonance Microscopy. *Clarendon Press* (1991).

A. Caprihan et al. "Flow Measurements by NMR". *Physics Reports 198* (1990), pp. 195–235.

A. G. Collins. "Properties of Produced Waters". *Petroleum Engineering Handbook*, H. B. Bradley, Ed., Chapter 24, pp. 24.1–24–23.

J. J. Dechter. *Progress in Inorganic Chemistry*, vol. 29 (1982), pp. 285–385.

J. R. Dyer. Applications of Absorption Spectroscopy of Organic Compounds. *Prentice–Hall* (1965), pp. 84–85.

T. C. Farrar et al. Pulse and Fourier Transform NMR. *Academic Press* (1971).

R. Freedman et al. "A New NMR Method of Fluid Characterization in Reservoir Rocks: Experimental Confirmation and Simulation Results". *SPE 63214*, Annual Technical Conference and Exhibition (Oct. 2000), pp. 1–15.

E. Fukushima et al. Experimental Pulse NMR. A Nuts and Bolts Approach. *Addison–Wesley* (1981).

Gerstein et al. "Transient Techniques in NMR of Solids". *Academic Press* (1985), pp. 240–248.

K. Halbach. "Design of Permanent Multipole Magnets with Oriented Rare Earth Cobalt Material". *Nuclear Instruments and Methods 169* (1980), pp. 1–10.

K. Halbach. "Physical and Optical Properties of Rare Earth Cobalt Magnets". *Nuclear Instruments and Methods 187* (1981), pp. 109–117.

J. P. Horkowitz et al. "Residual Oil Saturation Measurements in Carbonates with Pulsed NMR Logs". *SPWLA 36th Annual Logging Symposium* (Jun. 1995), Paper Q, pp. 1–12.

R. L. Kleinberg. "Well Logging". *Encyclopedia of Nuclear Magnetic Resonance*, vol. 8, (1996), pp. 4960–4969.

R. L. Kleinberg et al. "NMR Properties of Reservoir Fluids". *Log Analyst*, Nov.–(Dec. 1996), pp. 20–32.

R. L. Kleinberg et al. "Review: NMR Detection and Characterization of Hydrocarbons in Subsurface Earth Formations" *Spatially Resolved Magnetic Resonance* (1998), pp. 556–573.

J. C. M. Li et al. "Self–Diffusion Coefficient and Viscosity in Liquids". *J. Chem. Phys.*, vol. 23, No. 3. (Mar. 1955), pp. 518–520.

C. E. Morriss et al. "Hydrocarbon Saturation and Viscosity Estimation from NMR Logging in the Belridge Diatomite". *Log Analyst*, Mar.–Apr. 1997, p. 44–59.

L. Petrakis et al. "The Utilization of Nuclear Magnetic Resonance Spectroscopy for Petroleum, Coal, Oil Shale, Petrochemicals, and Polymers". Phenomenology, Paradigms of Applications, and Instrumentation *Applied Spectroscopy Reviews*, 15(2) (1972), pp. 195–260.

Prammer, M. G. et al. "A New Direction in Wireline and LWD NMR", *SPLA 43rd Annual Logging Symposium*, (Jun. 2002), pp. 1–11.

F. H. A. Rummens et al. "Intermolecular Interactions in Nuclear Magnetic Resonance". XI. The 13C and Proton Medium Shifts of CH4 in the Gas Phase and in Solution. *Canadian Journal of Chemistry* (1977), vol. 55, pp. 3021–3030.

Schlumberger Wireline Formation Testing and Sampling. SMP–7508 (1996); pp. 4–29 and 4–40.

J. M. Singer et al. "Fast NMR Logging for Bound Fluid and Permeability". *SPWLA 38th Annual Logging Symposium* (Jun. 1997), Paper YY, pp. 1–13.

C. Straley. "An Experimental Investigation of Methane in Rock Materials". *SPWLA 38th Annual Logging Symposium* (Jun. 1997), Paper AA, pp. 1–14.

B. P. Tissot et al. "Petroleum Formation and Occurrence". *Springer–Verlag* (1978), Fig. IV.1.20.

N. J. Trappeniers et al. "High Resolution Nuclear Magnetic Resonance Spectroscopy in Liquids and Gases at Pressures up to 2500 Bar". *Physica*, 82A (1976), pp. 581–595.

H. J. Vinegar et al. "Whole–Core Analysis by $^{13}$C NMR", *SPE Formation Evaluation 6*, (Jun. 1991), pp. 183–189.

Hurlimann, M. D. et al. *The Diffusion–Spin Relaxation Time Distribution Function as an Experimental Probe to Characterize Fluid Mixtures in Porous Media. Journal of Chemical Physics*, vol. 117, No. 22 (Dec. 8, 2002) pp. 10223–10232.

Hurlimann, M.D. et al. *Quantitative Measurement of Two–Dimensional Distribution Functions of Diffusion and Relaxation in Grossly Inhomogeneous Field. Journal of Magnetic Resonance*, vol. 157 (2002) pp. 31–42.s.

* cited by examiner

NUCLEAR MAGNETIC RESONANCE METHOD AND LOGGING APPARATUS FOR FLUID ANALYSIS

This patent application is a continuation in part of U.S. patent application Ser. No. 10/016,246 filed Oct. 30, 2001 which is a continuation-in-part of U.S. patent application Ser. No. 09/133,234 filed Aug. 13, 1998 (now issued U.S. Pat. No. 6,346,813). This patent application also claims priority from U.S. patent application Ser. No. 09/723,803 filed on Nov. 28, 2000 which is based on U.S. Provisional Application No. 60/170,121 filed on Dec. 10, 1999. All of these co-pending patent applications are incorporated by reference herein in their entireties.

FIELD OF THE INVENTION

The present invention relates to well logging tools and methods and, more particularly, to tools and methods for analyzing extracted formation fluids by nuclear magnetic resonance (NMR) techniques.

BACKGROUND

NMR has been a common laboratory technique for over forty years and has become an important tool in formation evaluation. General background of NMR well logging can be found, for example, in commonly owned U.S. Pat. No. 5,023,551 to Kleinberg et al., incorporated herein by reference in its entirety.

NMR relies upon the fact that the nuclei of many chemical elements have angular momentum ("spin") and a magnetic moment. In an externally applied static magnetic field, the spins of nuclei align themselves along the direction of the static field. This equilibrium situation can be disturbed by a pulse of an oscillating magnetic field (e.g., an RF pulse) that tips the spins away from the static field direction. The angle through which the spins are tipped is given by $\theta = \gamma B_1 t_p / 2$, where $\gamma$ is the gyromagnetic ratio, $B_1$ is the linearly polarized oscillating field strength, and $t_p$ is the duration of the pulse. Tipping pulses of ninety and one hundred eighty degrees are most common.

After tipping, two things occur simultaneously. First, the spins precess around the direction of the static field at the Larmor frequency, given by $\omega_0 = \gamma B_0$, where $B_0$ is the strength of the static field and $\gamma$ is the gyromagnetic ratio. For hydrogen nuclei, $\gamma/2\pi = 4258$ Hz/Gauss, so, for example, in a static field of 235 Gauss, the hydrogen spins would precess at a frequency of 1 MHz. Second, the spins return to the equilibrium direction according to a decay time, $T_1$, which is known as the spin-lattice relaxation time.

Also associated with the spin of molecular nuclei is a second relaxation time, $T_2$, called the spin-spin relaxation time. At the end of a ninety-degree tipping pulse, all the spins are pointed in a common direction perpendicular, or transverse, to the static field, and they all precess at the Larmor frequency. However, due to small fluctuations in the static field induced by other spins or paramagnetic impurities, the spins precess at slightly different frequencies, and the transverse magnetization dephases with a time constant $T_2$.

A standard technique for measuring $T_2$, both in the laboratory and in well logging, uses an RF pulse sequence known as the CPMG (Carr-Purcell-Meiboom-Gill) sequence. As is well known, after a wait time that precedes each pulse sequence, a ninety degree pulse causes the spins to start precessing. Then, a one hundred eighty degree pulse is applied that keeps the spins in the measurement plane, but causes the spins, which are dephasing in the transverse plane, to reverse direction and to refocus. By repeatedly reversing the spins using a series of one hundred eighty degree pulses, a series of "spin echoes" appear. The train of echoes is measured and processed to determine the irreversible dephasing, $T_2$.

In a uniform static magnetic field, each spin will experience the same magnetic field strength regardless of its position within the static field, and diffusion will not contribute to the observed relaxation rate, as defined in equation (1) below.

$$\frac{1}{T_2} = \frac{1}{T_{2,bulk}} + \frac{1}{T_{2,diffusion}} \tag{1}$$

In a magnetic field gradient, however, each spin will experience different magnetic field strengths as it diffuses through the static field. The Larmor frequencies of the diffusing spins become time dependent, and the series of one hundred eighty degree pulses cannot refocus the spins completely, leading to an additional decay signal. This additional decay signal is proportional to the diffusion coefficient, D, of the fluid and to the square of the gradient strength, g, and the square of the echo spacing, $t_E$, i.e., $$\frac{1}{T_{2,diffusion}} = \frac{1}{12} \gamma^2 g^2 D t_E^2. \tag{2}$$

Because the diffusion coefficient provides an indication of fluid type, measurement of the diffusion effects on the distribution of decay times $f(T_2)$ can be used as the basis for determining the characteristics of formation fluids.

Certain NMR measurements of diffusion involve changing the echo spacing, $t_E$, in a standard CPMG sequence, and thus, the amount of diffusion the spins undergo between echoes, and then comparing the measured relaxations. FIGS. 1A and 1B generally illustrate this approach. FIG. 1A shows two CPMG sequences with different echo spacings, $t_1$ and $t_2$, where $t_2$ is longer than $t_1$. As the echo spacing increases, the spins diffuse further between echoes, and the measured relaxation times will decrease depending on the diffusion coefficient of the fluid, as given in Equation 2 above. FIG. 1B shows the relaxation distributions, $f(T_2)$, for an oil and water determined from the two sets of echoes acquired from the two CPMG sequences illustrated in FIG. 1A. As seen in FIG. 1B, the relaxation distribution with the longer echo spacing, $t_2$, is shifted to lower relaxation times, $T_2$, relative to the relaxation distribution with the shorter echo spacing, $t_1$. The size of the shift is proportional to the size of the diffusion coefficient, as indicated by arrows 1 and 2. The shift of $f(T_2)$ for a fluid with a small diffusion coefficient 1, such as heavy oil, is smaller than the shift for a fluid with a larger diffusion coefficient 2, such as water or natural gas.

While such NMR diffusion measurements can be useful, they suffer from a number of drawbacks. For example, for a given acquisition time, the two CPMG sequences will not have the same number of echoes. The CPMG sequence with longer echo spacing will have a fewer number of echoes available and will suffer from lower signal to noise and lower data quality in general. In addition, relaxation distributions for different fluids often overlap, at least partially, making it difficult to identify shifts of individual relaxation times. In cases where the diffusion coefficients for different fluids are small, the shifts may be difficult to distinguish. Finally, these methods cannot separate out the contributions due to diffusion effects from bulk relaxation contributions in the observed relaxation distributions.

Accordingly, one object of the present invention is to provide a method and apparatus for determining characteristics of fluid using NMR techniques wherein effects from relaxation and diffusion may be measured separately.

SUMMARY OF THE INVENTION

The present invention provides a method and apparatus to determine characteristics of a fluid (such as a formation fluid or other fluid sample) using a diffusion edited NMR pulse sequence.

One embodiment of the present invention includes a method of extracting information about a fluid is disclosed comprising: a) obtaining a fluid sample; b) generating a sequence of magnetic field pulses in the fluid, the sequence comprising an initial magnetic field pulse, a first portion that follows the initial magnetic field pulse, and a second portion that follows the first portion; c) detecting magnetic resonance signals using the second portion of the sequence; d) modifying the first portion of the sequence, and repeating steps (b) and (c); and e) extracting information about the fluid by determining relaxation and diffusion characteristics and their correlation based on the signals detected in steps (c) and (d). The first and second portion of the sequence are defined relative to one another. For example, the first portion of the sequence is the arbitrary portion varied in step (d), while the second portion is the remaining portion of the sequence that is not varied in step (d).

Information obtained using this diffusion edited pulse sequence may be used to develop a two-dimensional function of two parameters indicative of the fluid.

In a second embodiment of the present invention, a method of extracting information about a fluid is disclosed comprising: a) obtaining a fluid sample; b) generating a first sequence of magnetic field pulses in the fluid, the first sequence comprising a first portion and a second portion; c) detecting magnetic resonance signals using the second portion of the first sequence; d) generating at least one other sequence of magnetic field pulses in the fluid, each other sequence comprising a third portion and a fourth portion, the third portion having a different sensitivity to diffusion effects than the first portion of the first sequence and the fourth portion having a similar sensitivity to diffusion effects as the second portion of the first sequence; e) detecting magnetic resonance signals using the fourth portion of each other sequence; and f) analyzing the detected magnetic resonance signals to separate diffusion effects from relaxation effects.

In a third embodiment, a method of extracting information about a fluid is disclosed comprising: a) obtaining a fluid sample; b) generating a first sequence of magnetic field pulses in the fluid, the first sequence comprising a first series of magnetic field pulses with a first time spacing; c) detecting spin echoes using the first series; d) generating a second sequence of magnetic field pulses in the fluid, the second sequence comprising a second series of magnetic field pulses with a second time spacing and a third series of magnetic field pulses with the first time spacing, the second spacing being greater than the first time spacing; e) detecting spin echoes using the third series; and f) extracting information about the fluid using spin echoes detected using the first series and spin echoes detected using the third series. This embodiment may include the steps of generating at least one other sequence of magnetic field pulses in the fluid, each other sequence comprising a fourth series of magnetic field pulses with a time spacing greater than the first time spacing and different from the second time spacing and from each other, and a fifth series of magnetic field pulses with the first time spacing; and detecting spin echoes using the fifth series, wherein information about the fluid is extracted using the spin echoes detected using the first series, the third series, and the fifth series.

In a fourth embodiment, a logging apparatus is disclosed comprising: a logging tool that is moveable through a borehole, wherein the logging tool is equipped with a fluid sampling means; and a processor that is coupled with the logging tool, the processor being programmed with instructions which, when executed by the processor causes the logging tool to: i) generate a sequence of magnetic field pulses in a fluid sample, the sequence comprising an initial magnetic field pulse, a first portion, and a second portion; ii) detect magnetic resonance signals produced from the fluid sample using the second portion of the sequence; iii) modify the first portion of the sequence and repeat steps (i) and (ii); and causes the processor to: iv) analyze magnetic resonance signals from a time relative to the initial magnetic field pulse and extract information about the fluid sample.

In a fifth embodiment, a logging apparatus is disclosed comprising: a logging tool that is moveable through a borehole, wherein the logging tool is equipped with a fluid sampling means; and a processor that is coupled with the logging tool, the processor being programmed with instructions which, when executed by the processor causes the logging tool to: i) generate a first sequence of magnetic field pulses in a fluid sample, the first sequence comprising a first portion and a second portion; ii) detect magnetic resonance spin echoes produced from the fluid sample using the second portion of the first sequence; iii) generate at least one other sequence of magnetic field pulses in the fluid sample, each other sequence comprising a third portion and a fourth portion, the third portion having a different sensitivity to diffusion effects than the first portion of the first sequence and the fourth portion having a similar sensitivity to diffusion effects as the second portion of the first sequence; iv) detect magnetic resonance spin echoes produced from the fluid sample using the fourth portion of each other sequence; and causes the processor to: v) analyze detected spin echoes to separate diffusion effects from relaxation effects.

In a sixth embodiment, a logging apparatus is disclosed comprising: means for sampling a formation fluid; means for generating a sequence of magnetic field pulses in a formation fluid sample, the sequence comprising an initial magnetic field pulse, a first portion and a second portion; means for detecting magnetic resonance signals using the second portion; means for modifying the first portion; and means for analyzing magnetic resonance signals from a time relative to the initial magnetic field pulse to extract information about the formation fluid.

In a seventh embodiment, a logging apparatus is disclosed comprising: means for sample a formation fluid; means for generating a first sequence of magnetic field pulses in the formation fluid sample, the first sequence comprising a first portion and a second portion; means for detecting magnetic resonance signals from the formation fluid sample using the second portion of the first sequence; means for generating at least one other sequence of magnetic field pulses in the formation fluid sample, each other sequence comprising a third portion and a fourth portion, the third portion having a different sensitivity to diffusion effects than the first portion of the first sequence and the fourth portion having a similar sensitivity to diffusion effects as the second portion of the first sequence; means for detecting magnetic resonance signals from the formation fluid sample using the fourth portion of each other sequence; and means for analyzing magnetic resonance signals to separate diffusion effects from surface and bulk relaxation effects.

Further details, features and embodiments of the invention will become more readily apparent from the detailed description that follows.

BRIEF DESCRIPTION OF THE FIGURES

The invention will be described in more detail below in conjunction with the following Figures, in which.

DETAILED DESCRIPTION

1. Diffusion Editing Technique

A NMR measurement according to the invention involves generating at least two different magnetic field pulse sequences in a fluid and detecting magnetic resonance signals produced by the different magnetic field pulse sequences. Information, such as saturation, diffusion coefficient, viscosity, composition, etc., about a fluid extracted from an earth formation is developed by analyzing the different magnetic resonance signals.

Generally speaking, the magnetic field pulse sequences used in the invention can be characterized as having two portions, a first portion followed by a second portion. In a NMR measurement according to the invention, the sensitivity of the first portion to diffusion effects in the presence of a magnetic field gradient is modified while the second portion remains substantially the same. Magnetic resonance signals are detected using the second portion and analyzed. Signals detected using the second portion, which is not changed, will exhibit substantially the same relaxation distribution from one magnetic field pulse sequence to the next, except that the amplitude of the signals will have been altered as a result of the first portion having been modified. By analyzing how the magnetic resonance signals change as the first portion is modified, information about the fluid may be extracted.

Stated another way, in the presence of a magnetic field gradient, the first portion of the magnetic field pulse sequences used in the invention are sensitive to both relaxation and diffusion effects whereas the second portion has substantially the same sensitivity to relaxation effects but reduced sensitivity to diffusion effects. Diffusion effects during the first portion introduce an extra decay into the signal detected using the second portion. The signal detected using the second portion is thus attenuated, or "diffusion edited" in proportion to the diffusion coefficient of the fluid (see Equation 2, above).

These diffusion effects may be detected in the presence of a static magnetic field gradient, or with the use of pulsed field gradients as described, for example, in commonly owned U.S. Pat. No. 5,796,252 to Kleinberg et al., incorporated herein by reference in its entirety. Pulsed field gradients introduced into the first portion of the magnetic field pulse sequences of the invention also may be used in conjunction with a static magnetic field to enhance these diffusion effects.

Figure 1A:
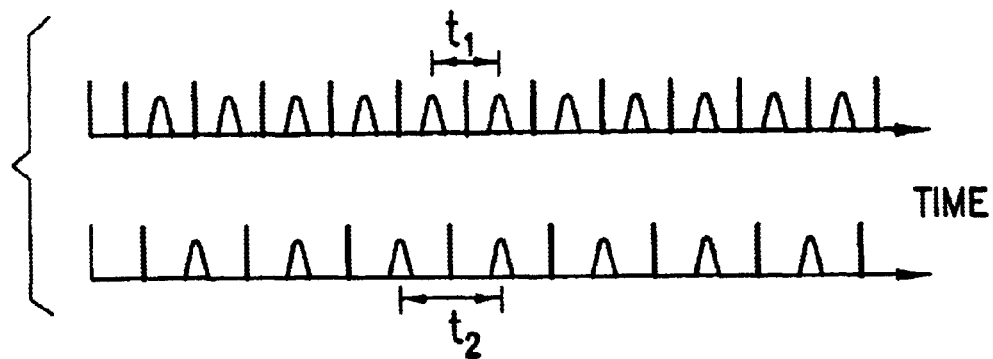
FIGS. 1A and 1B, taken together, illustrate a NMR measurement and $T_2$ distributions obtained therefrom according to the prior art.
Figure 1B:
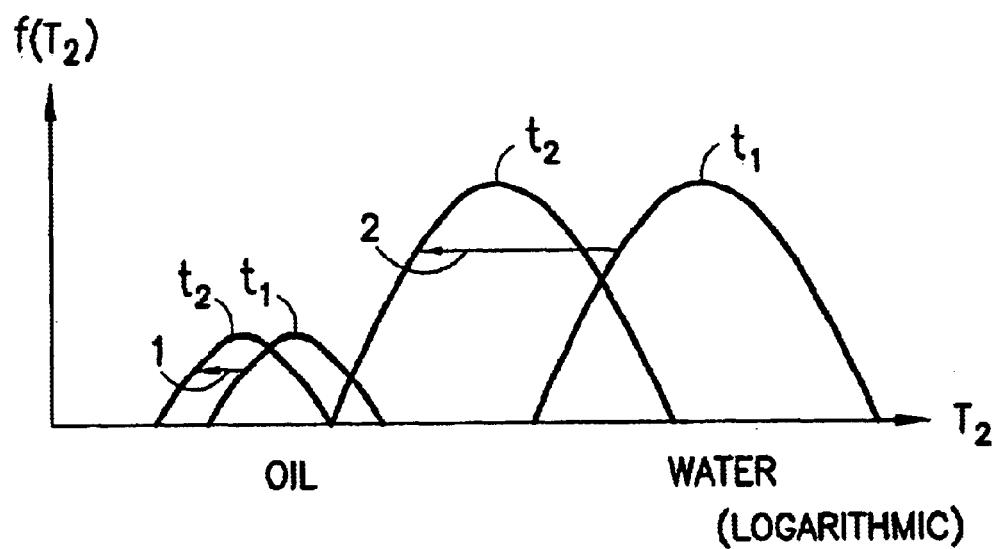
Figure 2A:
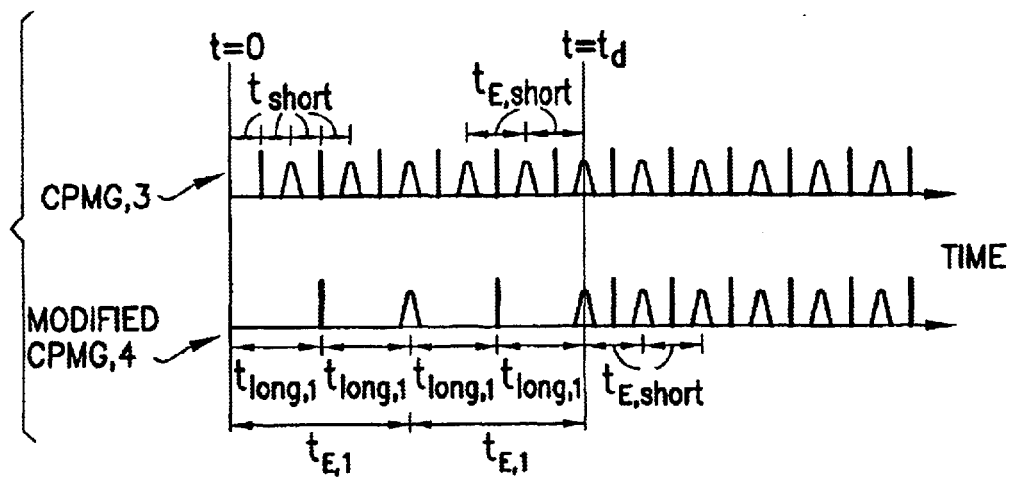
FIGS. 2A and 2B, taken together, illustrate one embodiment of a NMR measurement and $T_2$ distributions obtained therefrom according to the invention.
Figure 2B:
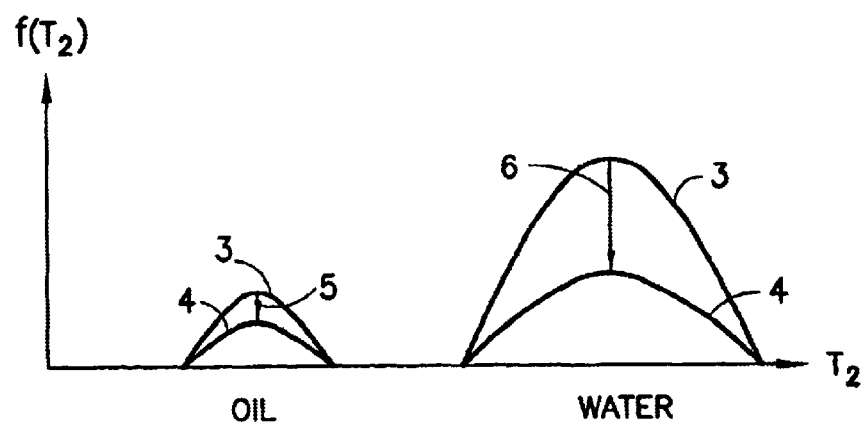

FIGS. 2A and 2B illustrate one embodiment of a NNR measurement according to the invention. After a static magnetic field is generated in a formation fluid sample, a first magnetic field pulse sequence 3 and then a second magnetic field pulse sequence 4 are generated in the fluid. The first sequence 3 in this embodiment (shown at the top of FIG. 2A) is a standard CPMG sequence in which an initial 90-degree pulse is followed, after a time $t_{short}$, by a series of 180-degree pulses separated in time by about $2t_{short}$. A magnetic resonance spin echo appears a time $t_{short}$ after each 180-degree pulse, producing a series of magnetic spin echoes with a time spacing, $t_{E,short}$, approximately equal to $2t_{short}$. This first sequence may be represented as:

$$90-[t_{short}-180-t_{short}-echo_i]_n \qquad (3)$$

where the time separating the echoes, $t_{E,short}$, is equal to about $2t_{short}$; $echo_i$ is the $i^{th}$ magnetic resonance spin echo; and n is the number of spin echoes in the sequence.

A standard CPMG sequence may be characterized as a magnetic field pulse sequence according to the invention in which the first portion is substantially identical to the second portion. A modified CPMG sequence according to the invention may be thought of as a CPMG sequence in which the first portion has been modified. The second portion of the modified CPMG sequence is not changed and so generates a CPMG-like series of magnetic resonance spin echoes with a time spacing approximately equal to $t_{E,short}$.

The second sequence 4 (shown at the bottom of FIG. 2A) is an embodiment of a modified CPMG sequence 4 in which the first few echo spacings of the standard CPMG sequence are elongated. An initial 90-degree pulse is followed by a first portion containing a first series of 180-degree pulses that begins a time, $t_{long,1}$, after the initial 90-degree pulse and are separated by about $2t_{long,1}$, where $t_{long,1}$, is greater than $t_{short}$. A magnetic resonance spin echo appears at a time $t_{long,1}$ after each 180-degree pulse, producing a first series of magnetic resonance spin echoes with a time spacing $t_{E,1}$ approximately equal to $2t_{long,1}$. The first portion is followed a second portion containing a second series of 180-degree pulses separated in time by about $2t_{short}$. The second series of 180-degree pulses begins at a time $t_{short}$ after the last spin echo of the first portion and refocuses this last spin echo to produce a second series of magnetic resonance spin echoes having a time spacing, $t_{E,short}$, which is equal to about $2t_{short}$.

The embodiment of a modified CPMG sequence 4 shown at the bottom of FIG. 2A may be represented generally as:

$$90-[t_{longj}-180-t_{longj}-echo_{kj}]_{mj}-[t_{short}-180-t_{short}-echo_{ij}]_{n'j} \quad (4)$$

where, for the $j^{th}$ sequence, $t_{longj}$ is greater than $t_{short}$; $echo_{kj}$ is the $k^{th}$ magnetic resonance spin echo of the first portion; (m,j) is the number of spin echoes of the first portion; $echo_{ij}$ is the $i^{th}$ magnetic resonance spin echo of the second portion; and (n',j) is the number of spin echoes of the second portion. As shown in FIG. 2A, the first portion of the modified CPMG sequence 4 contains two spin echoes, i.e., (m,j)=2; it will be appreciated, however, that the first portion may have other numbers of echoes.

Figure 3:
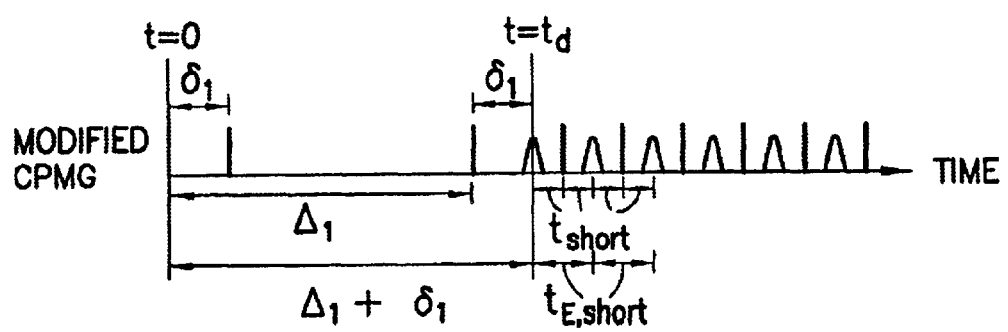
FIG. 3 shows a modified CPMG sequence that can be used in a NMR measurement according to embodiments of the invention.

Another embodiment of a modified CPMG sequence that may be used in accordance with the invention has a first portion that contains a stimulated echo sequence. For example, as shown in FIG. 3, the first portion includes a series of two 90-degree pulses at times $\delta_1$ and $\Delta_1$ after an initial 90-degree pulse, producing a stimulated echo at a time $(\Delta_1+\delta_1)$ after the initial 90-degree pulse. The second portion, which follows the first portion, contains a series of 180-degree pulses which begins a time $t_{short}$ after the last stimulated echo, refocusing the stimulated echo to produce a series of magnetic resonance spin echoes having a time spacing, $t_{E,short}$, which is equal to about $2t_{short}$. The overall sequence may be represented generally as:

$$90-[\delta_j-90-(\Delta_j-\delta_j)-90-\delta_j-echo_{kj}]_{mj}-[t_{short}-180-t_{short}-echo_{ij}]_{n'j} \quad (5)$$

where, for the $j^{th}$ sequence, $echo_{kj}$ is the $k^{th}$ stimulated echo of the first portion; (m,j) is the number of stimulated echoes of the first portion having an echo spacing equal to about $(\Delta_j+\delta_j)$; and $\delta_j$, $\Delta_j$, $t_{short}$, and indices (i',j) and (n',j) are as defined above.

Other embodiments of a modified CPMG sequence that may be used in accordance with the invention are described in commonly owned U.S. application Ser. No. 09/528,881, filed on Mar. 20, 2000, which is incorporated herein by reference.

The graph in FIG. 2B represents the relaxation distributions extracted from the magnetic resonance signals detected using the second portions of the first sequence 3 and the second sequence 4 in the presence of a magnetic field gradient. The relaxation distributions, $f(T_2)$, for an oil and water, shown in FIG. 2B are identical except that the amplitude of the second sequence signal 4 is attenuated relative to the amplitude of the first sequence signal 3. The amount of the signal attenuation is proportional to the size of the diffusion coefficient, as indicated by arrows 5 and 6. Thus, the signal attenuation for a fluid with a small diffusion coefficient 5, such as oil, is smaller than the signal attenuation for a fluid with a larger diffusion coefficient 6, such as water or natural gas. Measuring the relative change in amplitude between corresponding spin echoes from the first sequence and from the second sequence can yield quantitative information about the fluid sample under investigation.

Typically, the echo spacing in the second portion, $t_{E,short}$, is chosen to be as short as possible to increase the number, n, of spin echoes that can be generated and detected within a given acquisition time. This, in general, increases the signal-to-noise of the measured signal and, in the presence of a magnetic field gradient, reduces the sensitivity of the second portion to diffusion effects. Times for $t_{short}$ on the order of about 0.1 milliseconds (100 μs), leading to echo spacings, $t_{E,short}$, on the order of about 0.2 ms (200 μs), are currently used in well logging measurements, although the measurements of the invention may be made using other times for $t_{short}$ and $t_{E,short}$.

To properly correlate the spin echoes from the first sequence with the spin echoes from the second sequence, the data processing for both sequences starts at the same time, $t_d$, relative to the initial 90-degree pulse. In other words, spin echoes that precede $t_d$ are not used in processing, and only spin echoes starting from $t_d$ are analyzed. By beginning the data processing at the same time for each sequence, the magnetic resonance signals from each sequence will reflect substantially similar relaxation effects.

As shown in FIG. 2A, $t_d$ corresponds to the last echo of the first portion of the modified CPMG sequence. For example, with $t_{short}=0.1$ ms and $t_{longj}=4$ ms, data processing would start at $t_s=16$ ms, and if the two spin echoes of the first portion of the second sequence are disregarded, then the first 80 spin echoes of the first sequence, i.e., $echo_i$ from i=1 to $(mj) \times (t_{longj}/t_{short})$, would be disregarded. Data processing according to the certain embodiments of the invention, however, may include the last echo of the first portion, i.e., the echo from the first portion that is refocused by the magnetic pulses of the second portion. This means that the spin echoes that occur at $t=t_d$ would be included in the data processing.

Both sequences also may be truncated at the end during processing so a substantially equal number of spin echoes are analyzed and/or echoes with poor signal-to-noise are disregarded. Typically, both sequences still will contain a large number of echoes, particularly as compared to prior art techniques in which the echo spacing of a standard CPMG is increased. Thus, the methods of the invention will generally allow more precise measurements and provide better signal-to-noise as compared to prior art techniques.

A diffusion edited signal generated according to (4), for times greater than or equal to $t_d$, may be represented as:

$$M(t_{E,j}, t) = \int\int dD dT_2 f(D, T_2) \exp\left(-\frac{t}{T_2}\right) \exp\left(-\frac{(m, j)}{12} \gamma^2 g^2 D t_{E,j}^3\right), \quad (6)$$

where $t_d$ corresponds to the time (relative to the initial pulse) of the last echo of the first portion, $f(D,T_2)$ is the two-dimensional diffusion-$T_2$ probability density function, (m,j) is the number of echoes of the first portion, γ is the gyromagnetic ratio, g is the gradient field strength, D is the diffusion coefficient, and $t_{E,j}$ is the echo spacing in the first portion of the modified sequence. For modified sequences having more than one echo in the first portion, i.e., (m,j)>1, multiexponential diffusion decays may be observed over a broad detection bandwidth. Such multiexponential decay can be modeled more accurately by replacing the single exponential diffusion attenuation term in Equation 6 with multiple terms. For example, for (m,j)=2, two exponential terms, one from the direct echo and the other from the stimulated echo, would replace the single exponential term in Equation 6, yielding:

$$M(t_{E,j}, t) = \int\int dD dT_2 f(D, T_2) \quad (7)$$

$$\exp\left(-\frac{t}{T_2}\right)\left[A\exp\left(-\frac{1}{6}\gamma^2 g^2 Dt_{E,j}^3\right) + B\exp\left(-\frac{1}{3}\gamma^2 g^2 Dt_{E,j}^3\right)\right],$$

where A and B are parameters that depend only on the detection bandwidth.

Similarly, a diffusion edited signal generated according to (5), for times greater than or equal to $t_d$, may be represented as:

$$M_{t_d}(\delta, t) = \frac{1}{2}\int\int dD dT_2 f(D(t_d), T_2)\exp\left(-\frac{t}{T_2}\right)\exp(-\gamma^2 g^2 D(t_d) t_d \delta^2), \quad (8)$$

where $t_d$ is the time (relative to the initial pulse) of the stimulated echo, $f(D(t_d), T_2)$ is the two-dimensional diffusion-$T_2$ probability density function at time $t_d$, and $D(t_d)$ represents the diffusion coefficient at time $t_d$.

The amplitude of the detected echoes can be measured using any of various signal processing techniques known in the art and then, according to certain embodiments of the invention, fit to one of Equation 6, 7, 8, or other diffusion edited signal equations, depending on the magnetic pulse sequence used, in order to extract diffusion coefficient and other information about the fluid sample.

As previously suggested, measuring the relative change in amplitude between corresponding spin echoes from the first and second magnetic field pulse sequences can provide quantitative information about the formation fluid. In particular, a comparison of corresponding spin echoes can separate different contributions to the $T_2$ relaxation distribution, and so yield more accurate information about the formation fluid. For example, as discussed with regards to FIG. 2A, in the presence of a magnetic field gradient, the first portion of the modified CPMG sequences of the invention are more sensitive to diffusion effects than the second portion, leading to the signal from the second portion to be attenuated, or diffusion-edited, compared to the standard CPMG signal. However, the signal from the second portion exhibits the same bulk relaxation effects as, and is otherwise identical to, the signal from the standard CPMG sequence. Thus, taking a ratio of the amplitudes of the corresponding $T_2$ distributions of the first and second sequences separates diffusion effects from both surface and bulk relaxation effects.

Figure 4:
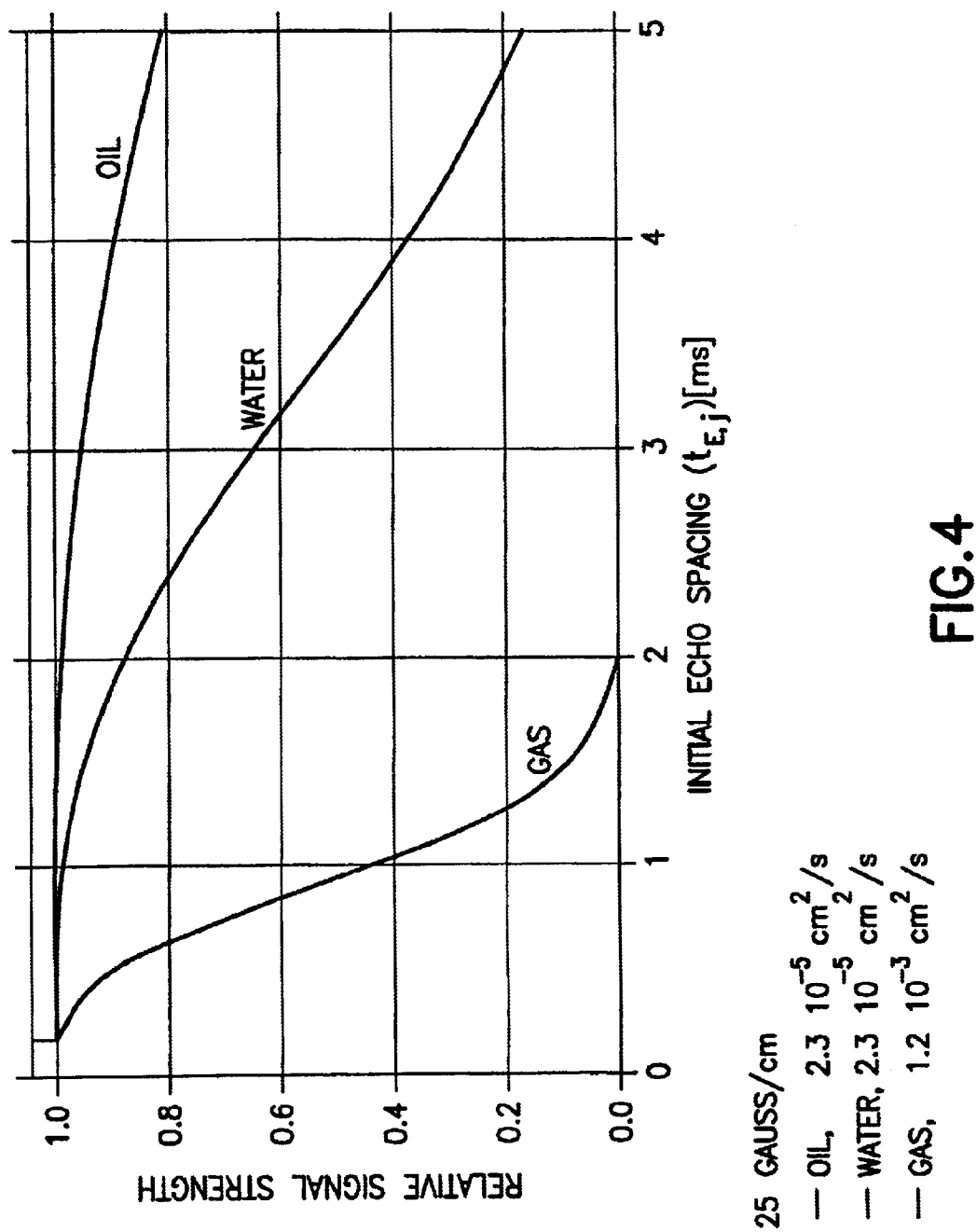
FIG. 4 is a graph of relative signal strength versus initial echo spacing for three different fluids according to certain embodiments of the invention.

For multiphase fluids, linear mixing laws govern the observed signal attenuation. Thus, components of the fluid having different diffusion coefficients may be differentiated by appropriately selecting and varying a time spacing in the first portion of the modified sequences (e.g., $t_{E,1}$; $\delta_j$ or $\Delta_j$). FIG. 4 contains a graph that may be useful in selecting a first portion time spacing. The graph shows approximate relative signal strength versus initial echo spacing, $t_{E,1}$, for oil (having a diffusion coefficient, $D_{oil}=2.3\times10^{-6}$ cm$^2$/s), water ($D_{water}=2.3\times10^{-5}$ cm$^2$/s) and gas ($D_{gas}=1.2\times10^{-3}$ cm$^2$/s) measured in a magnetic field gradient of about 25 Gauss/cm with a modified sequence generated according to (4), having two echoes in the first portion. Over a range of echo spacings of the first portion greater than approximately 0.8 ms, the relative attenuation of the gas signal is much larger than for either water or oil, indicating that this range may be useful in differentiating gas from water or oil. In general, an echo spacing of the first portion in a range of between about 0.5 to about 20 ms may be useful for hydrocarbon typing applications of the invention.

An echo spacing of the first portion to differentiate between two diffusing components may be approximated as:

$$t_{E,j} \approx \left[\frac{6\ln(D_+/D_-)}{\gamma^2 g^2(D_+ - D_-)}\right]^{1/3}, \quad (9)$$

where $D_+$ is the diffusion coefficient of the higher diffusing component, $D_-$ is the diffusion coefficient of the lower diffusing component, $\gamma$ is the gyromagnetic ratio and g is the magnetic field gradient strength. Equation (9) may provide a useful starting point in selecting an initial time spacing, if the different diffusing components (or a range of diffusion coefficients) are known or can be approximated a priori.

In some embodiments of the invention, the relative attenuation of the echo signal may be quantified in terms of an attenuation factor, $a_i$. The fluid composition then may be determined by taking a linear combination of the attenuation factors for the individual components. For example, the attenuation factor may be calculated as a ratio of the sums of all the measured echoes of a modified CPMG sequence to the measured echoes of a standard CPMG sequence, or as a ratio of initial amplitudes of a modified CPMG sequence to a standard CPMG sequence. In a gradient field of about 25 Gauss/cm and using a modified sequence generated according to (4) with two echoes in the first portion ($t_{E,1}=8$ ms, $t_{E,short}=0.2$ ms), an attenuation factor for bulk water, $a_w$, was calculated to be about 0.32 and for 6 cp oil, $a_{oil}$ was calculated to be about 0.85. For a fluid having water and oil components, the water saturation, $S_w$, i.e., the proportion of fluid that is water, can be determined from the measured attenuation factor of the fluid, $a_{meas}$, using the following relationship:

$$S_w = \frac{a_{oil} - a_{meas}}{a_{oil} - a_w}. \quad (10)$$

Figure 5:
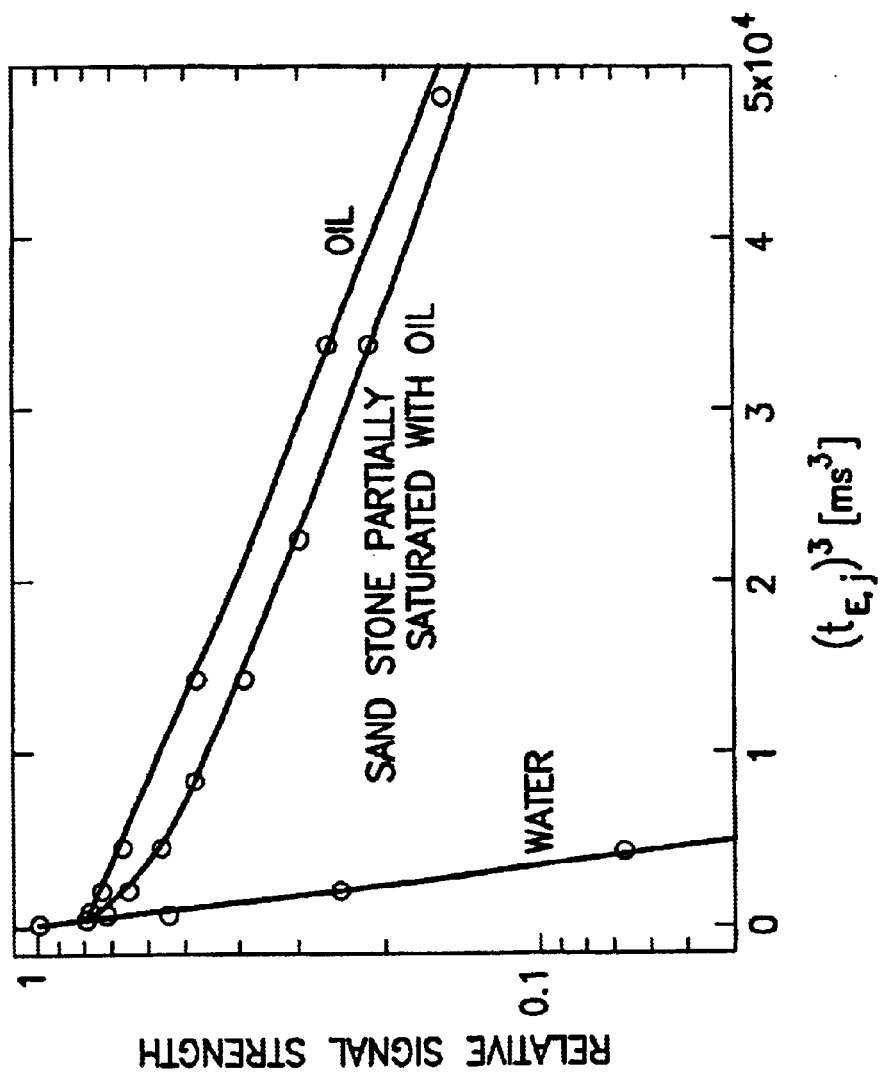
FIG. 5 is a graph showing relative signal strength for two samples as initial echo spacing is varied according certain embodiments of the invention.

According to other embodiments, the fluid composition can be determined by fitting the measured attenuation curve versus a first portion time spacing as a superposition of component curves. FIG. 5 shows the approximate relative initial signal strength of diffusion edited signals as an initial echo spacing is changed for a NiCl-doped water sample (labeled "water") and a S6 oil sample (labeled "oil"). The diffusion edited signals were generated in a uniform gradient field of about 13 Gauss/cm with a modified CPMG sequence according to (4) and having two echoes in the first portion. The plotted points, representing the amplitude of a modified CPMG signal relative to a standard CPMG signal, were fit to a curve using Equation 7 above, with A=0.59 and B=0.20. From the fit, the diffusion coefficients were extracted and found to be $D_w=2.5\times10^{-5}$ cm$^2$/s for the water sample and $D_{oil}=1.35\times10^{-6}$ cm$^2$/s for the oil sample.

The diffusion editing embodiments of the invention can extract saturation and diffusion coefficient information about a fluid directly without a priori knowledge of, and without having to make any assumptions about, relaxation in the fluid. As the measurements of these embodiments take place in the presence of a magnetic field gradient, the spin echoes are generated from a thin slice across the sample. By moving the sample and the gradient relative to one another along the gradient direction, an attribute profile of the fluid can be obtained. If pulsed gradients are used, the measurements are averages over the entire sample.

In other embodiments of the invention, a plurality of magnetic field pulse sequences, each with a different first portion (e.g., different time spacing, $t_{longj}$; or $\delta_j$ and/or $\Delta_j$), are used in making the NMR measurements. The diffusion edited magnetic resonance signal depends on a time spacing in the first portion (e.g., $t_{Ej}$; $\delta_j$, $\Delta_j$), so fluids with different diffusion coefficients will diffuse different amounts during different time spacings (see Equations 6, 7, or 8, above). Inverting data using only two different time spacings (as described in the embodiments above) yields an average diffusion coefficient for every relaxation time and so may not resolve different diffusing components that have overlapping relaxation times. Measuring magnetic resonance signals using more than two different time spacings allows diffusion coefficient and relaxation time to be extracted separately and so can help resolve different fluid components in terms of diffusion and relaxation, as well as other parameters that may be derived from D, $T_2$, or a combination of D and $T_2$, such as $T_1$, viscosity, saturation, etc.

Figure 6:
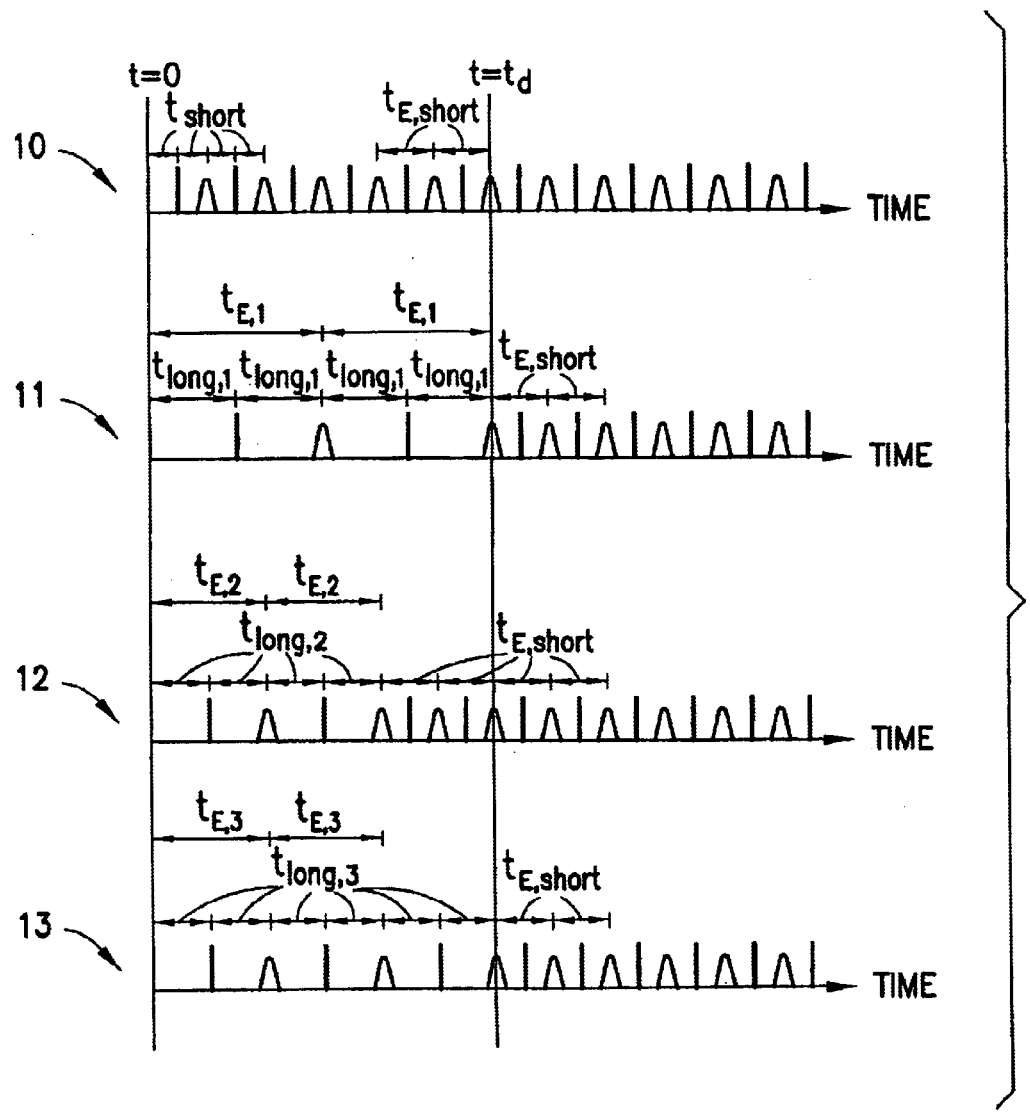
FIG. 6 illustrates a plurality of magnetic field pulse sequences that can be used in one embodiment of a NMR measurement according to the invention.

FIG. 6 illustrates a plurality of magnetic field pulse sequences that may be used in one embodiment of a NMR measurement according to the invention. A first magnetic field pulse sequence 10 is a standard CPMG sequence having a first time spacing, $t_{short}$, and a first echo spacing, $t_{E,short}$. A second magnetic field pulse sequence 11 is generated by modifying, in this case elongating, a time spacing between the initial 90-degree pulse and the first 180-degree pulse, $t_{long,1}$, leading to an elongated echo spacing, $t_{E,1}$, in the first portion. A third magnetic field pulse sequence 12 is generated by modifying a time spacing of the first portion again, $t_{long,2}$. A fourth magnetic field pulse sequence 13 is again generated by modifying a time spacing of the first portion, $t_{long,3}$, and also the number of spin echoes in the first portion.

This embodiment of a NMR measurement involves generating each of the magnetic field pulse sequences shown in FIG. 6 in a formation fluid sample. Magnetic resonance signals from each sequence are detected using the second portion of each sequence, which remains substantially the same from sequence to sequence. As discussed above, to properly correlate the spin echoes detected from each sequence, the data processing for each sequence starts at a time $t_d$ relative to the initial 90-degree pulse. FIG. 6 shows $t_d$ corresponding to the time of the last echo of the second sequence 11, which corresponds in this illustration with the time of the last echo of the fourth sequence 13. Some spin echoes from the second portion of the third sequence 12, which arise prior to time $t_d$, are discarded in the data processing according to this embodiment. The time $t_d$ need not necessarily correspond with the time of the last echo of the longest first portion, as shown in FIG. 6; however, $t_d$ typically is at least as long as the longest first portion.

Although FIG. 6 shows four magnetic field pulse sequences, other numbers of magnetic field pulse sequences may be used in NMR measurements according to the invention, with the use of more sequences resulting in higher resolution in the diffusion (or relaxation, viscosity, saturation, etc.) distribution. Additionally, the plurality of magnetic field pulse sequences need not include one type of modified CPMG sequence, as shown in FIG. 6. Measurements according to methods of the invention may be made using a plurality of magnetic field pulse sequences that includes a combination of modified CPMG sequences generated according to (4), (5) or any of the other sequences described in commonly owned U.S. application Ser. No. 09/528,881, incorporated herein by reference in its entirety.

The magnetic resonance signals from a plurality of magnetic field pulse sequences may be used to extract a two-dimensional function of any two parameters indicative of the formation fluid that can be transformed out of the data, such as D, $T_1$, $T_2$, viscosity, saturation, etc. From this two-dimensional function, one may choose to create a 3-D map. The measured data may include thousands of data points or, in some cases, tens of thousands of data points or more. In such cases, it may be helpful to compress the data before extracting information about the formation fluid.

The two-dimensional density function, $f(D,T_2)$, may be extracted from Equation 6, 7, or 8, above, using, for example, a least-squares optimization process and then plotted to generate a two-dimensional map of diffusion coefficient versus relaxation time. Other parameters, such as viscosity, saturation, etc., may be derived from D and/or $T_2$, and two such parameters mapped against one another to generate a two-dimensional map of, for example, $T_1$ versus $T_2$, viscosity versus saturation, etc.

Figure 7:
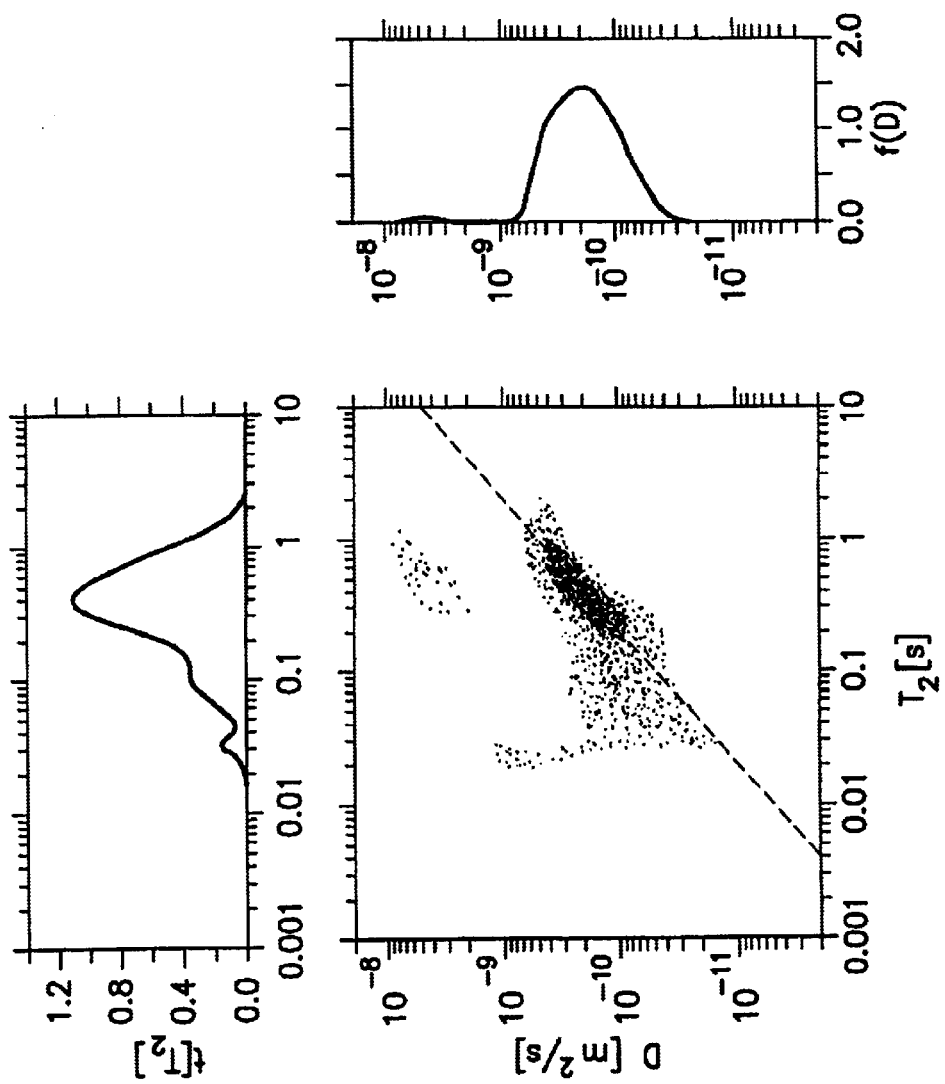
FIG. 7 shows a map based on the two-dimensional function of diffusion coefficient versus relaxation time according to certain embodiments of the invention.

FIG. 7 shows a full map based on the two-dimensional diffusion coefficient-relaxation time function, as well as corresponding one-dimensional diffusion and relaxation distributions. The NiCl-doped water had about the same relaxation time $T_2$ as the oil. Thus, in the conventional $T_2$ distribution shown on top (obtained by integrating $f(D,T_2)$ over D), the oil and water signals overlap completely and only a single peak appears. The map, as well as the diffusion distribution shown at the right (obtained by integrating $f(D,T_2)$ over $T_2$), clearly show two different diffusing components, one with a diffusion coefficient of around $10^{-6}$ cm$^2$/s that can be attributed to the S6 oil and the other with a higher diffusion coefficient of around $10^{-5}$ cm$^2$/s that can be attributed to water. The oil and water saturations correspond to the areas under the respective peaks, which were found to be 0.78 and 0.22, respectively (in good agreement with the results above).

Thus, according to one aspect of the invention, information such as diffusion coefficient and relative saturation of different components of a fluid may be determined, even if there is no contrast in relaxation times of the different components. As mentioned before, no assumptions or prior knowledge about the relationship between diffusion and relaxation are required to extract this information.

Figure 8:
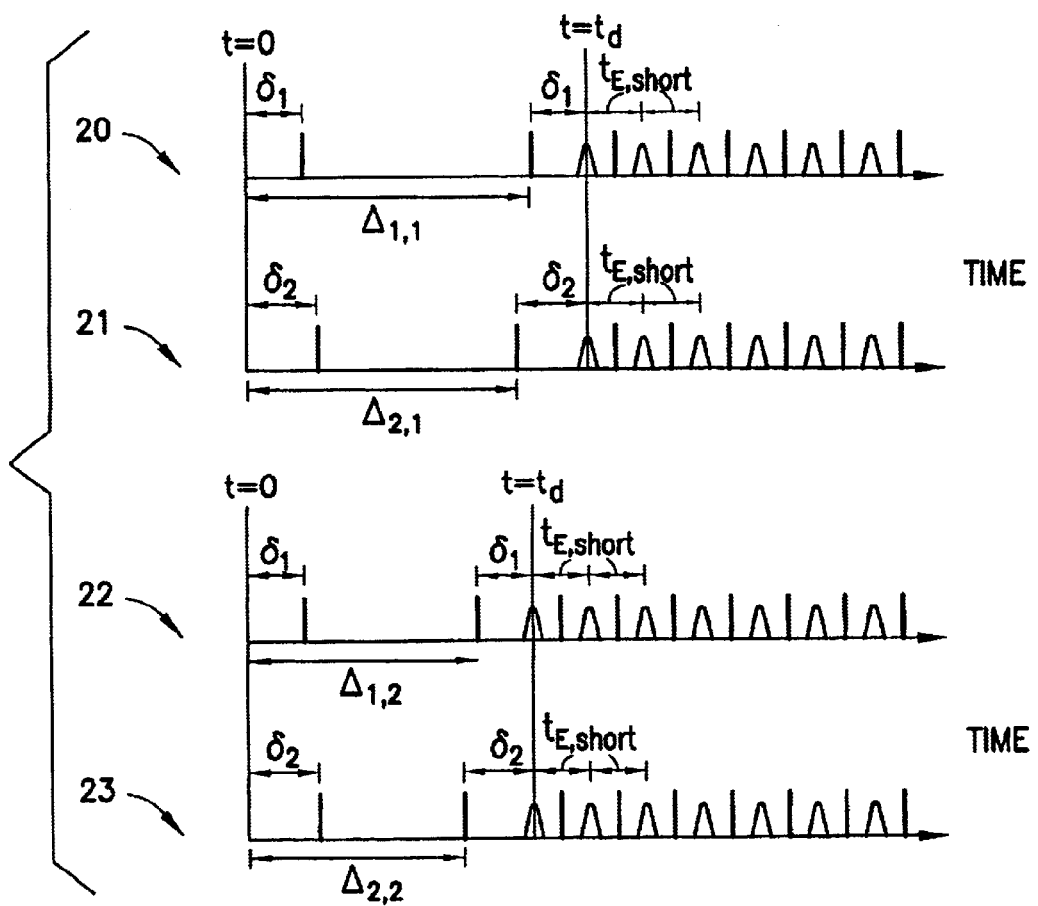
FIG. 8 illustrates a plurality of magnetic field pulse sequences that can be used in another embodiment of a NMR measurement according to the invention.

FIG. 8 illustrates a plurality of magnetic field pulse sequences that may be used in still another embodiment of an NMR measurement according to the invention. A first magnetic field pulse sequence 20 has a first portion that includes a first stimulated echo sequence. After an initial 90-degree pulse, a second 90-degree pulse is applied at time $\delta_1$ followed by a third 90-degree pulse at time $\Delta_{1,1}$, stimulating an echo at time $t_{d,1}$, all times being relative to the initial 90-degree pulse. A second magnetic field pulse sequence 21 is a second stimulated echo-modified CPMG sequence in which the time spacings between the initial and the second 90-degree pulses, $\delta_2$, and between the initial and third 90-degree pulses, $\Delta_{2,1}$, have been modified while the time at which a stimulated echo is produced, $t_{d,1}$, is held substantially constant. A third and a fourth magnetic field pulse sequences 22 and 23, respectively, are also stimulated echo-modified CPMG sequences. In the third magnetic field pulse sequence 22, the second 90-degree pulse is generated at a time $\delta_1$ after the initial pulse, as in the first sequence 20, but the time of the stimulated echo, $t_{d,2}$, has been modified, in this case shortened. The fourth magnetic field pulse sequence 23 stimulates an echo at substantially the same time, $t_{d,2}$, while the second 90-degree pulse is generated at a time $\delta_2$ after the initial pulse, as in the second sequence 21.

Referring to the embodiment illustrated in FIG. 8, in the presence of a magnetic field gradient, the amplitude of the stimulated echo at time $t_{d,i}$ will depend on $\delta_j$ (see Equation 8, above). Thus, measuring how the amplitude of the stimulated echo varies with $\delta_j$, allows an average diffusion coefficient, $D(t_{d,i})$, for all $T_2$ components at time $t_{d,i}$ to be extracted, and varying the time $t_{d,i}$ for each time spacing $\delta_j$ allows a time dependent diffusion coefficient, $D(t)$, to be determined. It should be appreciated that other modified CPMG sequences, as described above, may be used in time dependent measurements according to the invention, with analogous analyses applied.

2. Fluid Sampling Applications

Figure 9:
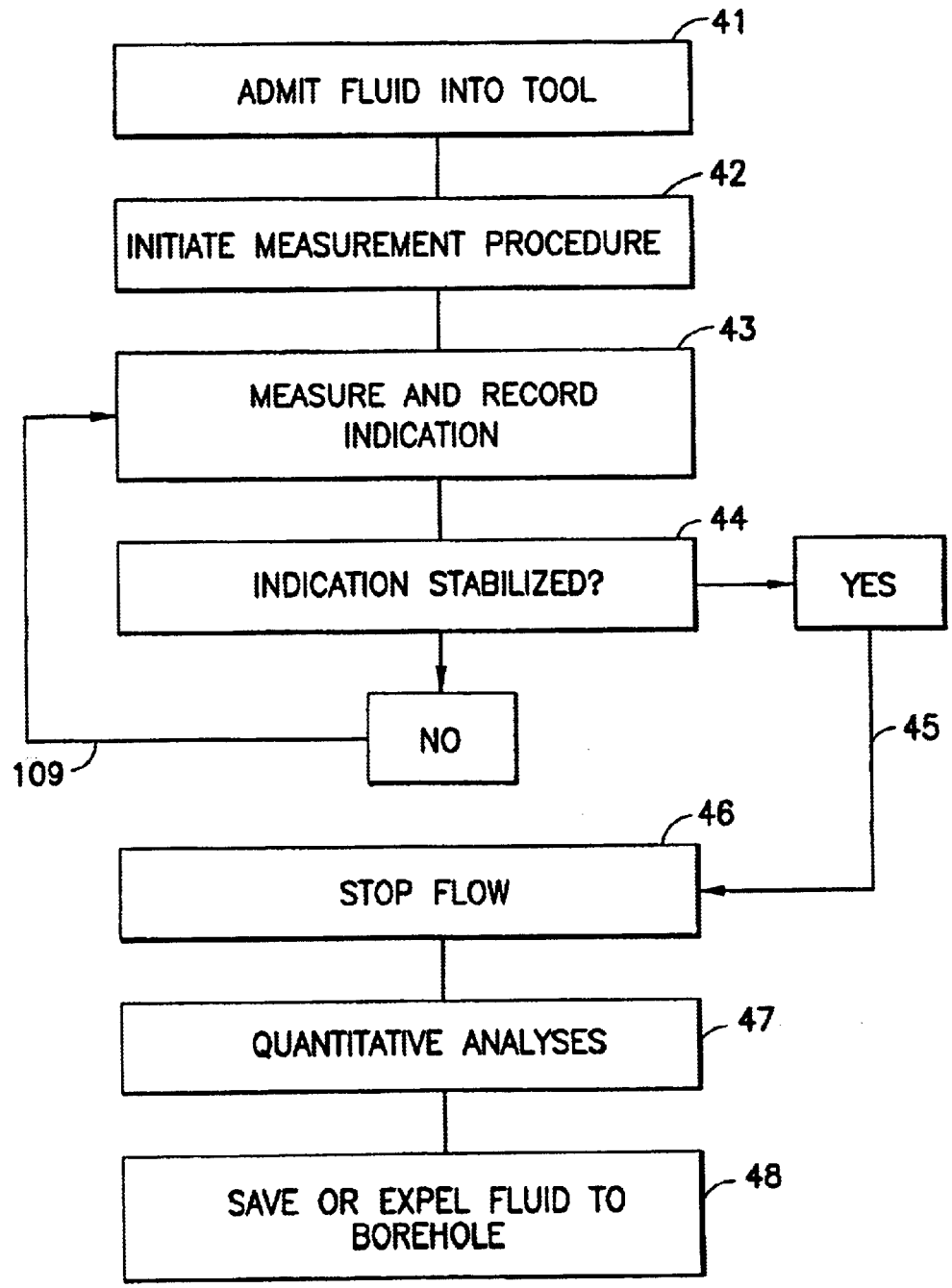
FIG. 9 is a flow chart depicting a typical measurement sequence.

A typical measurement sequence is shown in FIG. 9. Fluid is admitted into the tool flow line 41 and a measurement procedure initiated 42. An indication of magnetic resonance, of a group described below, is measured and recorded 43. While the indication changes with time, the measurement loop is continued 44; when the indication stabilizes 45, contamination has been reduced to a minimum. Alternatively, contamination in the fluid may be monitored by optical measurements of the fluid, as described, for example, in U.S. Pat. No. 6,274,865 to Schroer and Mullins. Then the flow is stopped or slowed 46 and quantitative analysis is undertaken 47. At the conclusion of the quantitative analysis, the fluid in the flow line is routed to storage bottles, or is expelled to the borehole. Alternatively, as mentioned above, some quantitative measurements may be made on the fluid without stopping or slowing its flow in the flow line, or a quantitative analysis may be made on a static fluid sample while diverting flow around the sample chamber.

There are a wide variety of measurements that can be used to monitor contamination, and another broad group of measurements that are useful in quantitatively analyzing fluid properties. Some of these are described below.

A. Contamination Monitoring Methods Using Diffusion Editing

Oil Base Mud Filtrate vs. Formation Oil

Many wells are drilled with muds in which oil is the continuous phase. These muds are comprised of hydrocarbons ("base oil"), typically hexadecanes, plus salt water, solids, and chemical additives. Usually only the base oil, together with oil-soluble additives, enter the formation and mix with formation oils. Water and solids remain in the borehole, or form a filter cake on the borehole wall. The oil entering the formation is called "oil base mud filtrate."

There are a number of NMR-detectable contrasts between oil base mud (OBM) filtrates and formation oils: (1) viscosity, (2) composition, (3) trace element content (natural or introduced), (4) diffusion coefficient, (5) proton density, and (6) molecular conformation. These contrasts may be enhanced using the diffusion edited pulse sequence described herein.

Figure 10:
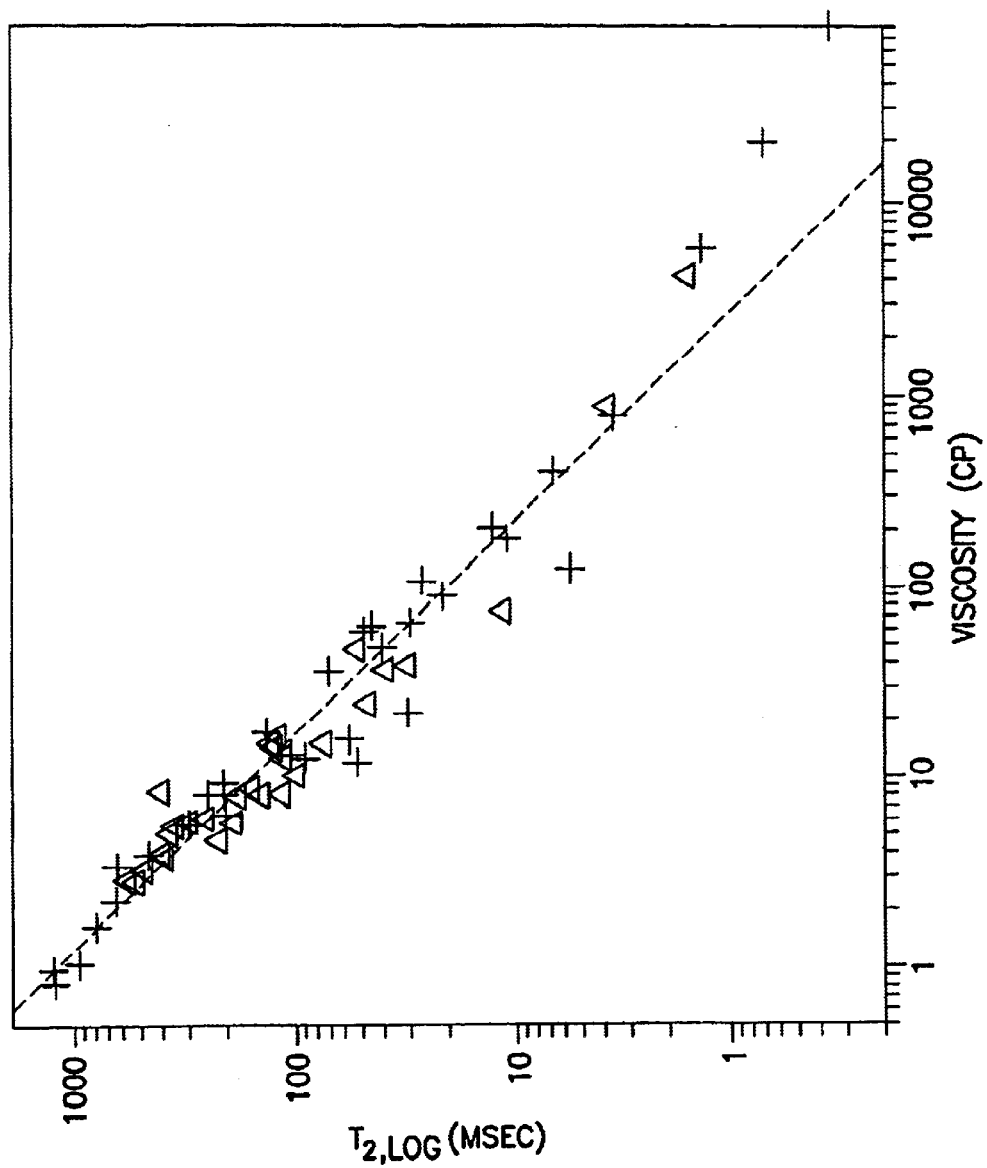
FIG. 10 is a graph depicting the logarithmic mean $T_2$ plotted versus viscosity for crude oils.

Viscosity: Extensive measurements on pure substances and crude oils have found an excellent correlation between fluid viscosity and the NMR relaxation times $T_1$ and $T_2$ as described in Bloembergen et al. "Relaxation Effects in Nuclear Magnetic Resonance Absorption," Physical Review 73, 679–712 (1948) and Morriss et al. "Hydrocarbon Saturation and Viscosity Estimation from NMR Logging in the Belridge Diatomite," Log Analyst, March–April 1997, pg 44–59, incorporated herein by reference in their entireties. Morriss et al. suggest that the logarithmic mean value of the relaxation time is strongly correlated with viscosity, see FIG. 10. Other relaxation time measures are also useful in qualitatively monitoring viscosity, including the time it takes for the NMR amplitude to fall to 1/e of its initial value.

In general, the viscosity of OBM filtrate is different (higher or lower) than that of the formation oil. Thus, measurements of NMR relaxation time can distinguish these fluids from one another. Moreover, when OBM filtrate is mixed with formation oil, the viscosity, and therefore relaxation time, of the mixture will be intermediate between the viscosities of the individual components. Because the diffusion edited sequence described herein allows for enhanced relaxation measurements, more accurate measurements of the fluids may be made.

As draw down continues, the time dependence of viscosity of the oil phase in the flow stream, $\eta(t)$, will vary as $$\eta(t)=\eta_{mf}+[(\eta_n-\eta_{mf})f(t)] \tag{11}$$

where $\eta_{mf}$ is the viscosity of the mud filtrate under downhole conditions, which can be measured in advance ill a laboratory if desired, and $\eta_n$ is the unknown viscosity of the native oil. f(t) depends on fluid and formation properties and is therefore unknown. However, f(t) is expected to be subject to the following conditions: $f(0) \geq 0$, $df/dt > 0$, $d^2f/dt^2 < 0$ (at least at long time), and $f(\infty) = 1$. Given a sufficiently long acquisition of data, $\eta_n$, can be estimated from the long-time asymptote of $\eta(t)$, and contamination level at any given time can be estimated.

Figure 11:
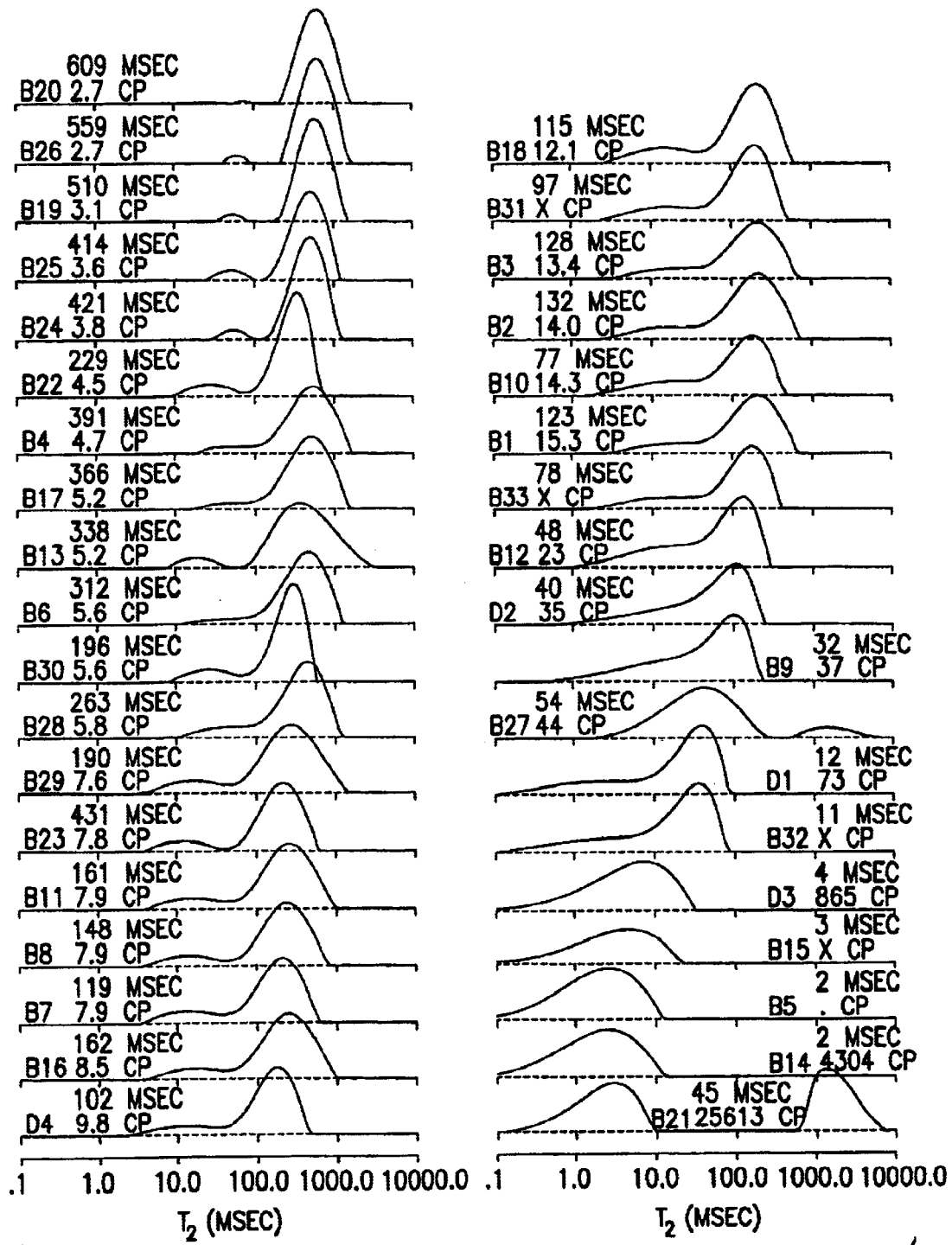
FIG. 11 shows $T_2$ distributions for a number of crude oils having a variety of physical properties.

Relaxation Time Distribution: Oil base mud filtrates are characterized by a narrow distribution of relaxation times. In contrast, crude oils have broad distributions of relaxation times, see FIG. 11 and Morriss et al., "Hydrocarbon Saturation and Viscosity Estimation from NMR Logging in the Belridge Diatomite," Log Analyst, March–April 1997, pg 44–59, incorporated herein by reference in its entirety. Thus, even if the OBM filtrate and native crude have the same viscosity, NMR $T_1$ and/or $T_2$ analysis can distinguish them based on the width of the distribution of relaxation times. Using the diffusion edited sequences of the present invention, more accurate measurements of relaxation time distribution may be made.

Trace Element Content: Trace elements can be detected in two ways: (1) the paramagnetic ions or compounds dissolved in liquids shorten the NMR relaxation times of liquid protons; and (2) the quantity of certain other nuclear or electronic species can be measured directly by resonance measurements of those species.

Dissolved paramagnetic compounds will reduce the proton relaxation times of oils. Thus, if two oils have the same viscosity, they will have different relaxation times if they have substantially different paramagnetic content. While many crude oils and most oil base mud filtrates have negligible magnetic content, some crude oils have significant amounts of vanadium or nickel, as described in Tissot and Welte, "Petroleum Formation and Occurrence," Springer-Verlag, 1978, Figure IV. 1.20, incorporated herein by reference in its entirety. Because the relaxation effect is proportional to paramagnetic concentration, the proportions of two oils in a mixture can be monitored. Deliberate introduction of an oil-soluble paramagnetic substance into the oil base mud can considerably enhance this effect when the native crude is relatively free of paramagnetic material.

NMR-active nuclei can be monitored directly to determine contamination levels. OBM filtrates may differ from native oils by having substantially different concentrations of oxygen, sulfur, or nitrogen. Of these, nitrogen is the best NMR target because its NMR-active form, $^{14}N$, has good NMR sensitivity and a reasonable natural abundance, see Table 1 below. Considerably greater sensitivity to contamination can be attained if trace elements are mixed with the drilling mud to mark the filtrate. For example, a fluorine-labeled organic compound can be detected directly by measuring the 19F resonance.

TABLE 1

NMR Properties of Elements Common in Oilfield Fluids

| Isotope | Frequency Frequency($^1$H = 1) | Natural Abundance | NMR Sensitivity[1] | Net Sensitivity[2] |
|---|---|---|---|---|
| $^1$H | 1 | 1.00 | 1 | 1 |
| $^{13}$C | 0.251 | 0.011 | $1.59 \times 10^{-2}$ | $1.75 \times 10^{-4}$ |
| $^{14}$N | 0.072 | 0.996 | $1.01 \times 10^{-3}$ | $1.01 \times 10^{-3}$ |
| $^{19}$F | 0.941 | 1.00 | 0.83 | 0.83 |

[1] At 100% abundance, $^1$H = 1
[2] At natural abundance, $^1$H = 1

NMR Amplitude: Hydrogen NMR amplitude is controlled by hydrogen index and the effect of incomplete polarization:

$$S = V_{water} \times HI_{water} \times [1 - \exp(-W/T_{1water})] + \\ V_{oil} \times HI_{oil} \times [1 - \exp(-W/T_{1oil})] + \\ V_{gas} \times HI_{gas} \times [1 - \exp(-W/T_{1gas})] \quad (12)$$

where $V_{water}$, $V_{oil}$, and $V_{gas}$ are the relative volumes of water, oil, and gas in the NMR measurement section of the flow line. HI is the hydrogen index (proton density relative to pure water). W is the effective polarization time of the measurement (i.e., the wait time between pulse sequences).

Oils with API gravity greater than 20, and with no dissolved gas, have proton density equal to that of water, see Vinegar et al., "Whole Core Analysis by $^{13}$C NMR," SPE Formation Evaluation 6, 183–189 (June 1991), incorporated by reference herein in its entirety. Most oil mud filtrates also have hydrogen densities equal to that of water. Gas is always a formation fluid; it is never a part of mud filtrates. A reduced proton density indicates gas, which is anticorrelated with the presence of mud filtrate in the flow line.

Light Oil and Gas/Oil Base Mud Filtrate: This is the most important contamination detection problem, and the one the optical fluid analyzer has the most trouble with. In this case, native oil has a longer relaxation time than OBM filtrate. Thus, as the proportion of native fluid increases, the proton signal amplitude will decrease. The presence of free gas associated with native oil accentuates the contrast. Signal level will stabilize at a low level when OBM contamination has been eliminated.

Water Base Filtrate vs. Formation Water

Trace Element Content: Diffusion edited NMR measurements can also help distinguish water base mud (WBM) filtrate from formation water. There will be little or no contrast in viscosity, diffusion coefficient, proton density, or molecular conformation. However, the trace element content can be considerably different. Water soluble paramagnetic ions (either natural of introduced) will have a strong relaxing effect, which can be used to monitor proportions of filtrate and connate water.

The use of chromium lignosulfonate muds, or manganese tracers used for formation evaluation, see Horkowitz et al., 1995 SPWLA Paper Q, incorporated by reference herein in its entirety, add paramagnetic ions to the filtrate. These ions reduce the filtrate relaxation time. Thus, they increase contrast with light oils and gas, and decrease contrast with medium to heavy oils.

NMR is sensitive to sodium, so if filtrate and connate water have different salinity, sodium concentration provides a good measure of contamination. The apparatus described herein can make diffusion edited NMR measurements of sodium by retuning the antenna to the appropriate resonance frequency.

Oil vs. Water

Oil and water can be distinguished by many of the same techniques outlined above. Proton relaxation time differences may be based on viscosity, diffusion coefficient, paramagnetic relaxation agents, or NMR-visible trace elements. The water phase will have a very narrow relaxation time distribution in contrast to crude oil, which often has a broad distribution. This distribution may be enhanced using the diffusion edited pulse sequence described herein.

Light Oil and Gas/Water Base Mud Filtrate: Water-based mud filtrates often have relaxation times intermediate between oil-based mud filtrates and native oils. Thus, the contrast in hydrogen signal amplitude is somewhat reduced as compared to oil/oil-based mud filtrate. However, hydrogen amplitude can still be used to monitor water-based mud filtrate contamination using the diffusion edited sequence described herein, especially in the presence of formation gas which depresses the total signal as water contamination diminishes.

C. Quantitative Fluid Characterization with NMR

A downhole NMR instrument installed in fluid sampling tools can make some of the most important measurements now being made in fluid analysis laboratories. The purpose of the downhole measurements is to provide means of making a partial analysis when the sample is taken, after which the sample can be saved for further analysis or discarded to the borehole. In this manner an unlimited number of fluid samples can be analyzed on each trip in the hole. The measurements are made at formation temperature and pressure, after minimum manipulation, thus helping to ensure sample integrity. Transportation and disposal problems are minimized or eliminated.

Nuclear magnetic resonance (NMR) is a powerful fluid characterization technique. The volumes of individual components of fluid mixtures, and some physical properties of each component, can be measured. The method is inherently noninvasive and noncontacting.

The physical properties of formation fluid are determined quantitatively by making a measurement when it has been determined that contamination is reduced to an acceptable level. Alternatively, fluids can be characterized by measuring their physical properties during mud filtrate clean up, and extrapolating the results to zero contamination level.

Volume Fractions

The calibrated NMR signal from a mixture of gas, oil, and water is $$S = V_{water} \times HI_{water} \times [1 - \exp(-W/T_{1water})] + \\ V_{oil} \times HI_{oil} \times [1 - \exp(-W/T_{1oil})] + \\ V_{gas} \times HI_{gas} \times [1 - \exp(-W/T_{1gas})] \quad (13)$$

where $V_{water}$, $V_{oil}$ and $V_{gas}$ are proportional to the volumes of each fluid. HI (hydrogen index) is the proton density for each fluid, normalized to the proton density of water at 20° C. and 1 atmosphere pressure. The last factor on each line is a correction to account for polarization time W, which is the wait time between pulse sequences.

Water, oil, and gas signals can be separated by methods described below. To obtain the fluid volumes from resolved NMR signals, the hydrogen index must be determined. The situation is different for each fluid. For charts of hydrogen index, see R. L. Kleinberg, H. J. Vinegar, Log Analyst, November–December 1996, pg. 20–32, incorporated herein by reference in its entirety.

Water: $HI_{water}$ is defined to be unity at room temperature and pressure; the effects of elevated temperature and pressure are tabulated, see Amyx, Bass and Whiting, Petroleum Reservoir Engineering, 1960, pg 458, incorporated herein by reference in its entirety. A larger correction to $HI_{water}$ is due to salinity. Thus, the salt content of the water must be known to obtain an accurate volume. The solubility of natural gas in water is low, and therefore does not have a significant effect on hydrogen index.

Oil: For oil at room temperature and pressure, without dissolved gas, hydrogen index is unity for API gravity greater than 20, see H. J. Vinegar et al., "Whole Core Analysis by 13C NMR," SPE Formation Evaluation, 6, 183–189 (1991), incorporate herein by reference in its entirety, which is the range of interest for fluid sampling tools. $HI_{oil}$ will track density as a function of temperature and pressure. There is no generally accepted correlation between $HI_{oil}$ and dissolved gas content.

Gas: $HI_{gas}$ is in the range of 0–0.6 for oilfield conditions, so the gas signal is not negligible. $HI_{gas}$ is a known function of temperature and pressure, which are measured by fluid sampling tools, and chemical composition, which is not. Carbon dioxide has no proton NMR signal, and thus may be obtained by difference when the volumes of water, oil, and natural gas are measured directly. At high flow rates, however, gas will not polarize significantly and will provide minimal NMR signal. One may then use an independent density measurement such as x-ray to determine the presence of gas.

Relaxation Time Analysis

Water and Oil in the Absence of Gas: Water in the tool flow line at downhole temperature and pressure will have relaxation times of several seconds. The magnetization decay of crude oils is multiexponential, but when the downhole viscosity of oil is greater than a few centipoise, water and oil NMR signals have distinctly different relaxation times, see R. L. Kleinberg, H. J. Vinegar, Log Analyst, November–December 1996, pg. 20–32, incorporated by reference herein in its entirety. This enables oil and water signals to be separated using a $T_1$ or $T_2$ distribution, particularly the diffusion edited pulse sequence described herein. If the water and oil signals are well resolved in the $T_1$ or $T_2$ distribution, in the absence of free gas, the areas under the peaks are equal to $$V_{water} \times HI_{water} \times [1 - \exp(-W/T_{1water})] \quad (14a)$$

and $$V_{oil} \times HI_{oil} \times [1 - \exp(-W/T_{1oil})] \quad (14b)$$

respectively, where W is the effective polarization time, as described previously.

The acquisition of a string of echoes via the diffusion edited pulse sequence described herein allows one to determine the $T_2$ of a sample. Once the time-domain data has been acquired, existing inversion methods can be used to determine a $T_2$ distribution. $T_1=T_2$ for liquids in the flow line apparatus, so if $T_2$ is measured by the CPMG pulse sequence, the polarization correction can be accurately computed.

Gas Measurements: The relaxation time of gas is a function only of its temperature and pressure, which are measured. For free gas in the absence of magnetic field gradients, $T_1=T_2$, in the range of several seconds, and the decay is single exponential, as described in C. Straley, "An Experimental Investigation of Methane in Rock Materials," SPWLA 38th Annual Logging Symposium, 1997, Paper AA, incorporated by reference herein in its entirety. Thus, the decay time of free gas can coincide with water and light oil.

Gas is distinguished from liquids by its diffusion coefficient. The diffusion edited sequence described herein may be useful in this measurement.

Carbon NMR

Carbon may be found in some formation waters, as carbonate or bicarbonate ion, but it predominates in oil and gas. Thus, in many cases, a measurement of carbon amplitude gives a direct measurement of hydrocarbon quantity. The NMR-active isotope of carbon is $^{13}C$, which has a natural abundance of about 1%. At natural abundance, $^{13}C$-NMR visibility is about $1.75 \times 10^{-4}$ that of $^1H$ (see Table 1 above). Also, $^{13}C$ relaxation times tend to be long ($T_1$ for carbon ranges from hundreds of milliseconds to seconds for oils with API gravity greater than 20 or viscosity less than 100 cp), making signal accumulation slow.

$^{13}C$ NMR measurements can be made with the diffusion edited pulse sequence described herein. Successive scans may be stacked and summed to improve the signal-to-noise ratio (SNR). Summing over each echo in time (or, equivalently, looking at the dc component of each echo in frequency space) can further improve SNR. Additional SNR improvement may result from inclusion of proper filtering.

With such improvements in SNR, it is estimated that a H/C ratio may be determined with an error of about 4.8% in less than 5 minutes. Cross-polarization with hydrogen is expected to give a further reduction in error. See Gerstein and Dybowski, Transient Techniques in NMR of Solids, 1985, incorporated by reference herein in its entirety.

Oil Viscosity

Oil viscosity can be determined if the oil signal is resolved from other fluid signals, such as by using the diffusion editing technique described above. Also, oil viscosity can be related to the oil's diffusion coefficient, which may be measured using techniques described previously.

When relaxation analysis is used, $T_1$ or $T_2$ is measured directly. As stated above, crude oils have broad distributions of relaxation times. However, it has been found that oils with low viscosity relax more slowly than those with higher viscosity, see C. E. Morriss, R. Freedman, C. Straley, M. Johnston, H. J. Vinegar, P. N. Tutunjian, in Transactions of the SPWLA 35th Annual Logging Symposium, 1994 and Log Analyst, March–April 1997, pg 44, incorporated by reference herein in its entirety. A single relaxation time parameter which captures the viscosity dependence is the logarithmic mean (see also FIG. 10):

$$T_{2LM} = \exp\left[\frac{\sum_i m_i \log_e(T_{2i})}{\sum_i m_i}\right] \quad (15a)$$

$$T_{1LM} = \exp\left[\frac{\sum_i m_i \log_e(T_{1i})}{\sum_i m_i}\right]; \quad (15b)$$

It has been found that over the range 1 cp to 300 cp, and in the absence of an applied magnetic field gradient, $T_{1LM}$ and $T_{2LM}$ (in seconds) are related to viscosity $\eta$ (in centipoise):

$$T_{2LM} = \frac{1.2}{\eta^{0.9}}, \text{ at 2 MHz} \quad (16a)$$

$$T_{1LM} = \frac{1.1}{\eta^{0.5}}, \text{ at 85 MHz.} \quad (16b)$$

As described above, improved $T_1$ and $T_2$ measurements may be made using the diffusion edited pulse sequence of the present invention.

Relation of oil viscosity, gas-oil ratio, stock tank API gravity and relaxation rates: Downhole oil viscosity may be obtained from NMR relaxation rates using the diffusion edit sequence described herein with a correction for gas/oil ratio (GOR):

$$T_{1LM} = T_{2LM} = \frac{aT}{\eta_0 f(GOR)}, \quad (17)$$

where T is the absolute temperature, $\eta_0$ is the crude oil viscosity at downhole temperature and pressure, $\alpha$ is an experimentally determined parameter with a value of 0.004 s.cp.K$^{-1}$ for a wide variety of crude oils at 2 MHz, and GOR is defined as m$^3$ solution gas per m$^3$ stock tank liquid at standard conditions (60° F., 1 atm), see R. Freeman, et al., "A New NMR Method of Fluid Characterization in Reservoir Rocks: Experimental Confirmation and Simulation Results," SPE Annual Technical Conference and Exhibition, SPE 63214 (2000), incorporated by reference herein in its entirety. The empirically determined $f(GOR)$ is given by:

$$f(GOR) = 10^{10\alpha} \quad (18),$$

where $$\alpha = -0.127(\log_{10}(GOR))^2 + 1.25\log_{10}(GOR) - 2.80 \quad (19).$$

Alternatively, $f$GOR) may be fit to the following polynomial expression:

$$f(GOR) = 1 + (3.875 \times 10^{-3})GOR - (5.3736 \times 10^{-7})GOR^2 \quad (20).$$

GOR may be determined, for example, using an optical fluid analyzer, such as Schlumberger's OFA, which can make optical measurements on a fluid in the flow line. Near-infrared (NIR) absorptions of methane (CH$_4$), a principal component of downhole gas, can be distinguished from those of methylene (—CH$_2$—), a dominant component of oil, and the two correlated to GOR. See U.S. Pat. No. 5,939,717 issued Aug. 17, 1999, incorporated herein by reference in its entirety.

Once GOR and downhole viscosity are known, one may also calculate stock tank API gravity. The stock tank (i.e., standard surface condition, 60° F., 1 atm) API gravity (or density) of crude oil is an important determinant of its price, and is therefore of fundamental interest to an operator in the field. Determining a stock tank property under downhole conditions requires use of fluid property correlations, which are well-established.

Figure 12:
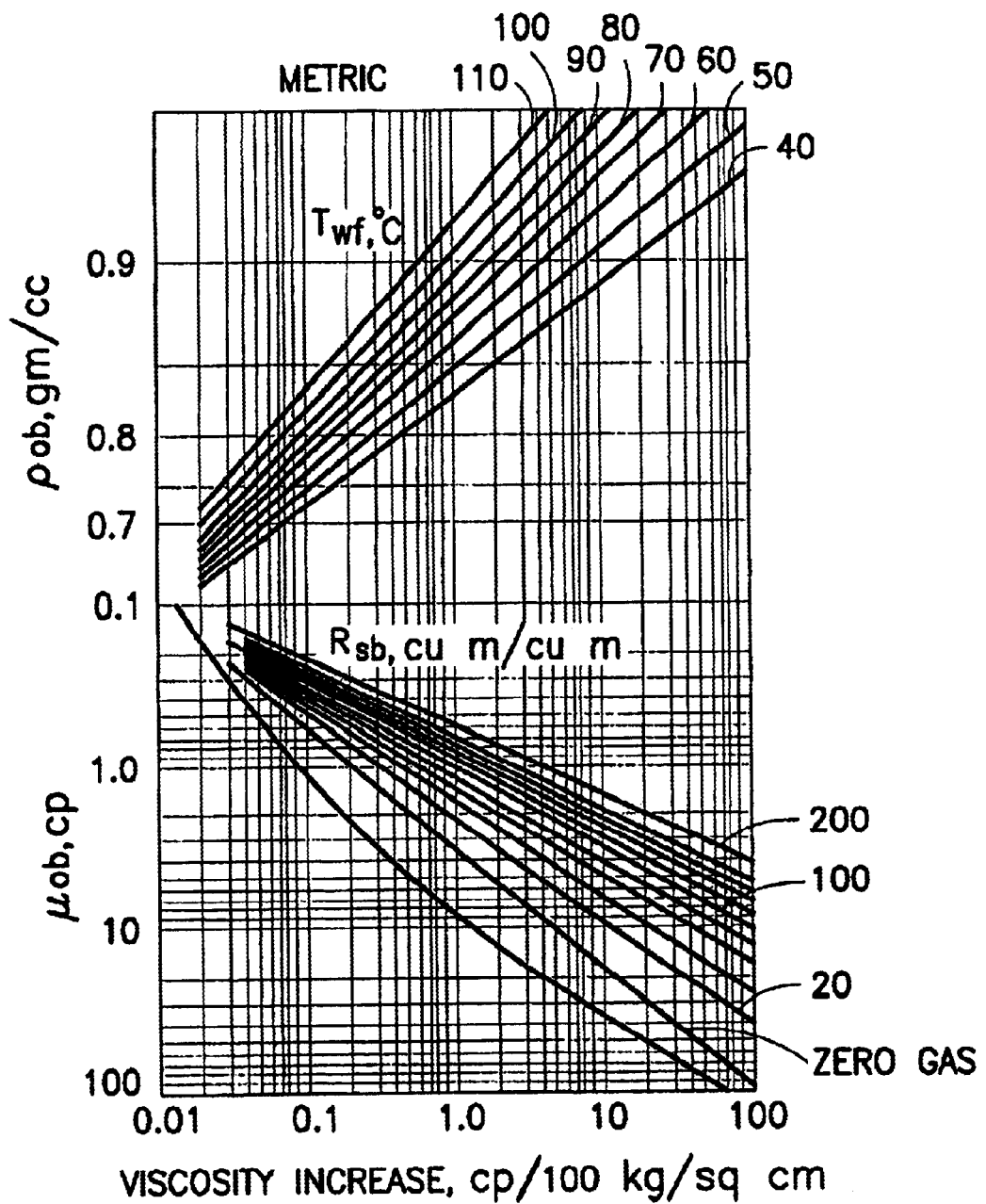
FIG. 12 is a fluid correlation chart in accordance with the present invention.

One such correlation relates stock tank API gravity to downhole fluid temperature (which is typically measured with downhole sampling tools, such as the MDT), GOR, and viscosity. Once downhole viscosity, GOR, and temperature have been measured, the stock tank API gravity can be determined using a fluid correlation chart, such as that shown in FIG. 12. The lower vertical axis of the chart marks viscosity. A horizontal line is extended from the viscosity value measured by diffusion edited NMR to a curve associated with the GOR determined by optical analysis (or other means). From the point at which the viscosity value intersects with the GOR curve, a vertical line is extended to the curve associated with the fluid temperature. From that point of intersection with the temperature curve, a second horizontal line is extended to the upper vertical axis, which marks the stock tank API gravity value. In practice, these steps are carried out by a computer.

Oil Composition

One of the primary products of conventional fluid analysis is oil composition. There are two methods by which diffusion edited NMR can provide at least a partial composition relaxation time analysis. The relaxation time depends on correlation times due to molecular motion, see Bloembergen, Purcell and Pound, Physical Review 73, 679 (1948), incorporated by reference herein in its entirety. Protons in large molecules tend to move slower, and hence relax faster, than those in small molecules. Crude oils are mixtures of pure hydrocarbons, and have broad distributions of relaxation times, see C. E. Morriss, R. Freedman, C. Straley, M. Johnston, H. J. Vinegar, P. N. Tutunjian, in Transactions of the SPWLA 35th Annual Logging Symposium, 1994; Log Analyst, March–April 1997, pg 44, incorporated by reference herein in its entirety. Oil type is determined by comparing relaxation time distributions obtained in the fluid sampling tool to a catalogue of such distributions compiled from laboratory data.

3. Apparatus

Figure 13:
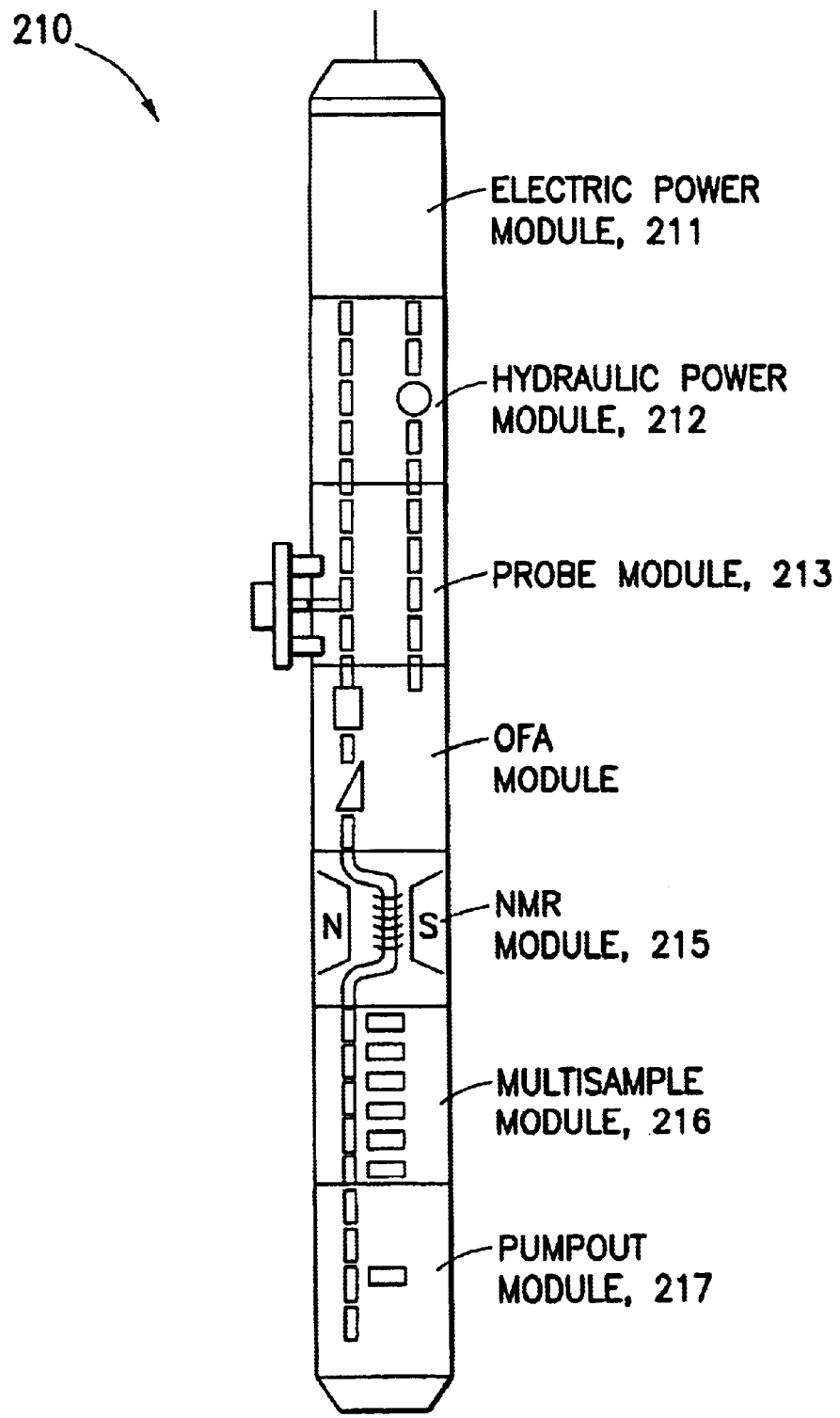
FIG. 13 is a schematic diagram of one embodiment of a fluid sampling tool utilized in extracting formation fluid.

The NMR methods described above may be used in fluid sampling tools, such as Schlumberger's Modular Dynamics Testing Tool (MDT). In general, modern fluid sampling tools are composed of several parts which enable extraction of fluids from permeable earth formations. Referring to FIG. 13, with the tool identified by 210, the following modules are in the prior art, see *Schlumberger Wireline Formation Testing and Sampling*, SMP-7058 (1996), published by Schlumberger Wireline and Testing, incorporated by reference herein in its entirety: the electric power module 211 and the hydraulic power module 212 power the tool; the probe module 213 is deployed so as to make a hydraulic seal with the formation; and the pumpout module 217 lowers the pressure in the flow line in a controlled manner so as to extract fluid from the formation while maintaining the pressure near the original formation pressure. Samples are optionally monitored by an optical fluid analyzer (OFA) 214 and are retained for transportation to surface laboratories in the multisample module 216.

The NMR module which is the subject of this invention is shown at 215 in FIG. 13. It is built around the flow line, and provides no obstructions to the flow of fluid within the tool.

Figure 14:
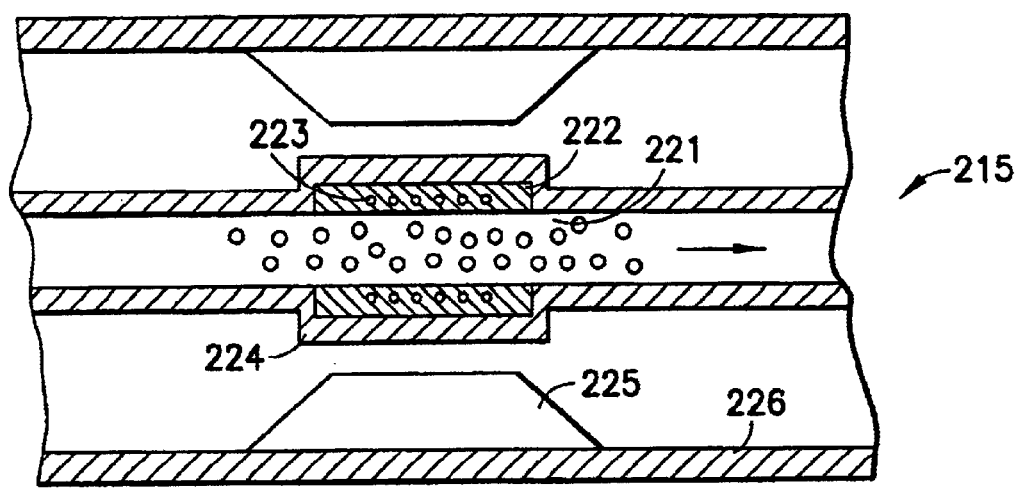
FIG. 14 is a schematic axial section of a flow line NMR apparatus.
Figure 15:
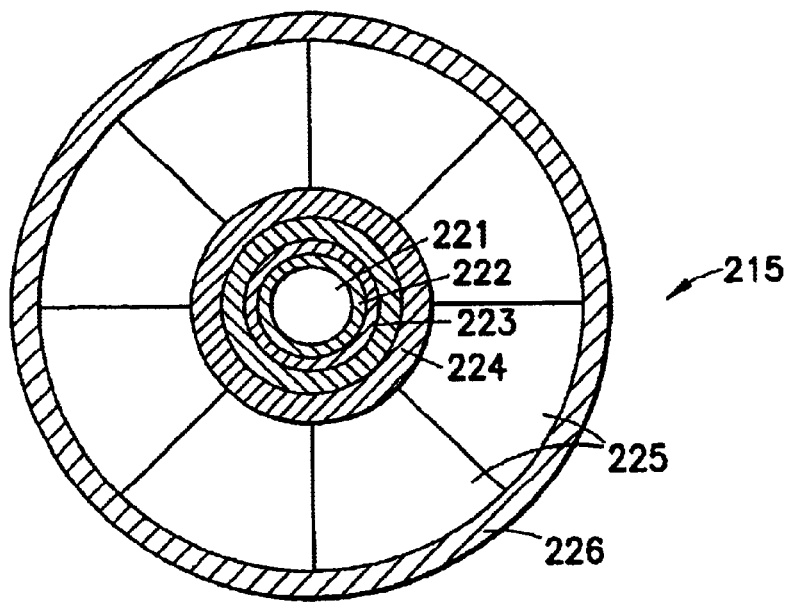
FIG. 15 is a cross-sectional view of the apparatus of FIG. 13.

More detailed drawings of one configuration of a diffusion edited NMR apparatus 215 are shown in FIGS. 14 and 15. Fluid withdrawn from the formation flows through a flow channel 221. In non-instrumented sections of the tool, the channel is defined by a thick-wall metal tube 224 capable of withstanding formation pressure of at least 20,000 pounds per square inch.

In the NMR-instrumented section of the flow line, the channel is defined by the inside diameter of an antenna support 222. The antenna support 222 must be made of a nonconductive and preferably nonmagnetic material. The antenna support 222 must be capable of resisting chemical attack by formation fluids. It must also be capable of resisting erosion by solids which may enter the flow line from the formation or borehole. Ceramics or hard polymeric materials are suitable materials for the antenna support 222.

The NMR antenna 223 is embedded in the antenna support 222. The NMR antenna 223 must be capable of radiating magnetic field at the Larmor frequency, typically 40 MHz. This radiated magnetic field is conventionally called B$_1$ (as discussed above). In one illustrative implementation, the NMR antenna 223 is a solenoidal coil which generates an oscillating magnetic field parallel to the axis of the flow channel 221. The B$_1$ field need not be particularly uniform over the volume of the flow channel 221.

The antenna support 222 is enclosed by an enlarged portion of thick-wall metal tube 224, so as not to obstruct the flow channel 221. The tube 224 and antenna support 222 are able to contain the high pressure formation fluids in the flow channel 221. High frequency magnetic fields cannot penetrate metals, so the NMR antenna 223 must be placed inside the metal tube 224 of the flow line 221.

An array of permanent magnets 225 is placed outside the thick-wall metal tube. These create a constant magnetic field, conventionally called $B_o$, substantially perpendicular to the $B_1$ field generated by the antenna. To make chemical shift measurements $B_o$ is preferably substantially uniform in the volume occupied by fluid. However, to measure relaxation time, diffusion coefficient, or spin density of hydrogen or other elements, $B_o$ need not be particularly uniform. One suitable arrangement of permanent magnets is described by Halbach, see K. Halbach, Nuc. Inst. Methods 169, 1–10 (1980) and K. Halbach, Nuc. Inst. Methods 187, 109–117 (1981), incorporated by reference herein in their entireties.

The entire NMR apparatus is enclosed in a sonde housing 226 which is attached to other similar housings in the tool string lowered into the well.

Gradient coils (not shown) can also be provided for the purpose of making pulsed field gradient measurements of diffusion coefficient and other quantities. If the static magnetic field is aligned with the z-axis, the most effective gradients are $dB_z/dx$, $dB_z/dy$, and $dB_z/dz$. A $dB_z/dz$ gradient can be generated by a pair of saddle coils potted together with the coil which provides the $B_1$ field. Prescriptions for designing saddle coils that generate maximally uniform gradients can be found in the literature, see R. Turner, "Gradient Coil Systems," Encyclopedia of Nuclear Magnetic Resonance, 1996, incorporated by reference herein in its entirety.

Figure 16A:
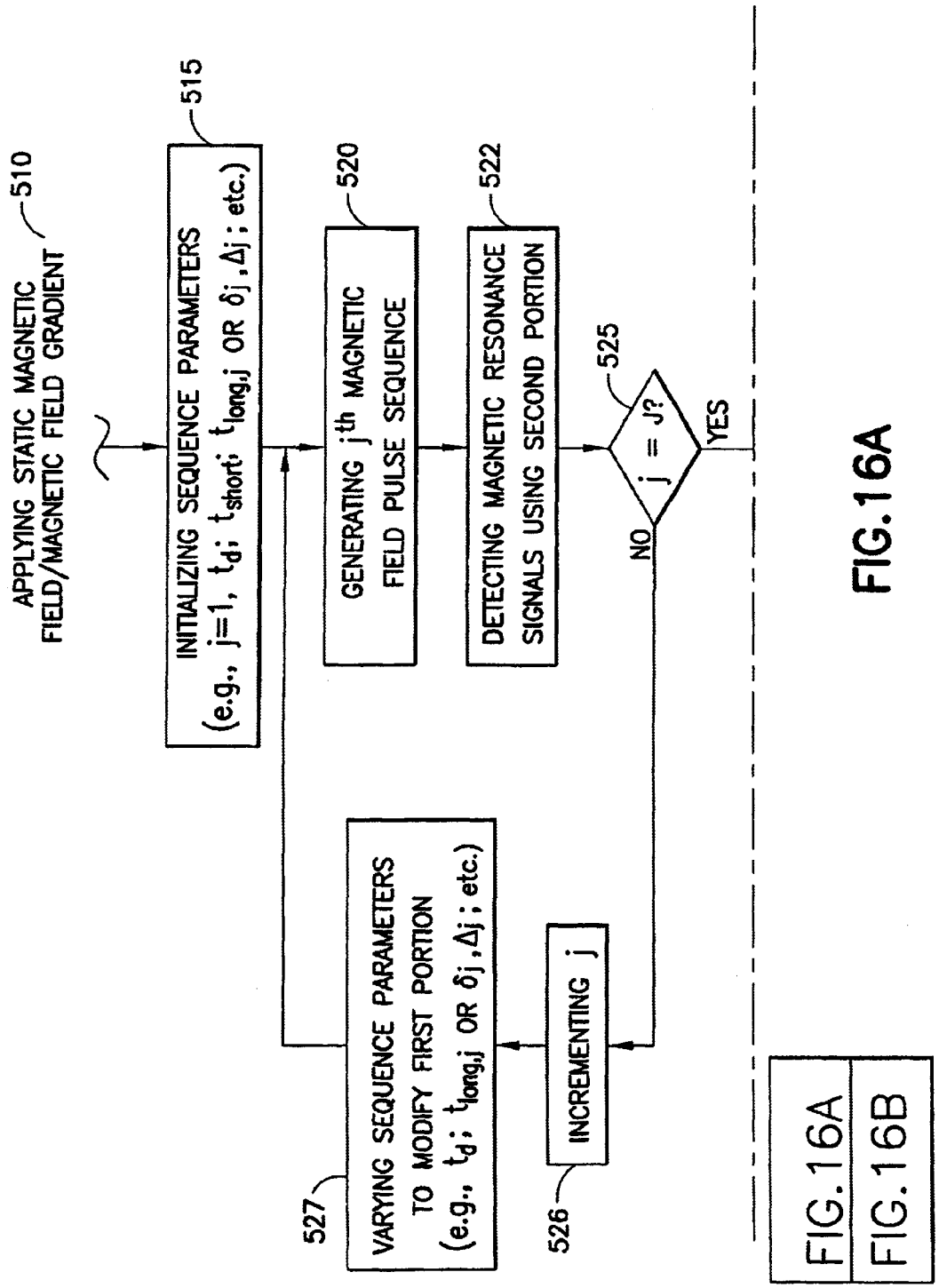
FIGS. 16A/B is a flow diagram of a routine that can be used in programming a processor or processors in implementing certain embodiments of the invention.
Figure 16B:
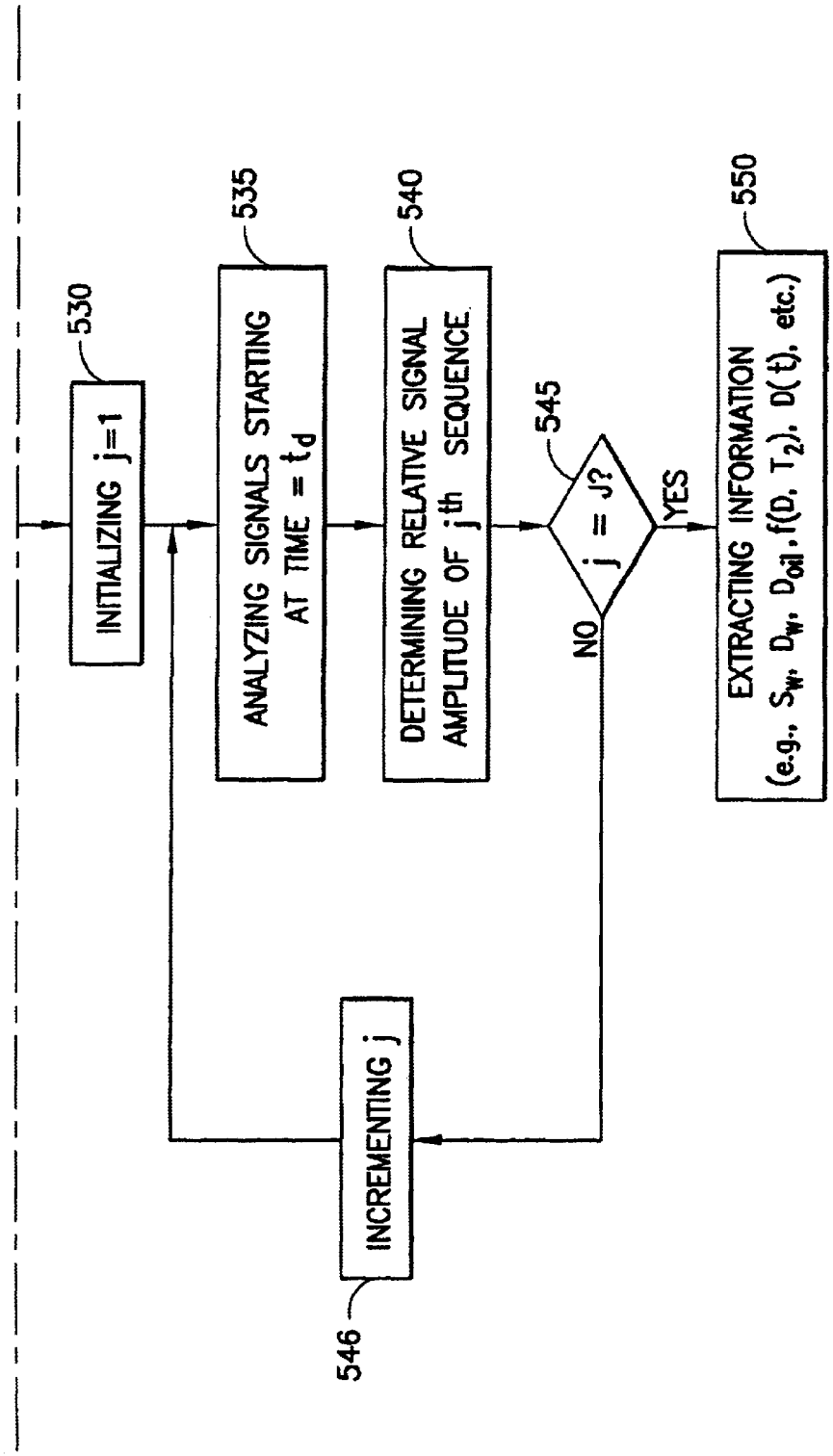

Embodiments of the invention may be implemented with logging devices, such as those described above, without the need for any hardware modifications. FIGS. 16A/B shows a flow diagram of a routine that can be used in programming a processor in implementing embodiments of the invention. The routine may be stored on or provided over a computer or machine readable medium, such as read-only memory (ROM); random access memory (RAM); magnetic disc or tape; a CD-ROM or other optical storage media; electrical, optical, acoustical or other forms of propagated signals; and the like. The processor may be a downhole processor, an uphole processor, or a combination thereof The processor also may include a remote processor that may be used for implementing some of the data interpretation parts of the routine.

Prior to the beginning of the programmed routine and as shown at 510, a static magnetic field and, for certain embodiments, a static magnetic field gradient are applied to a formation fluid sample. The static magnetic field and field gradient typically are applied using a logging tool having a permanent magnet or an array of permanent magnets, as described above. Logging tools can typically generate static magnetic field gradients in a range of about 10 to 80 Gauss/cm, but embodiments of this invention may be implemented with gradients outside this range.

The programmed routine begins at block 515, which represents initializing parameters for the magnetic field pulse sequences used in the invention. The sequence parameters may include, for example, $j=1$, $t_{short}$, $t_d$, $t_{longj}$ or $\delta_j$ and $\Delta_j$, depending on the pulse sequence to be applied. Other sequence parameters may be used instead of, or in addition to, the parameters listed (for example, a number (m,j) may be used to track the number of spin echoes in the first portion, an index, $i=1$, may be initialized to track different times $t_{d,i}$, etc.), and the sequence parameters may be initialized all together or at different points in the routine as needed.

Generating a magnetic field pulse sequence in the formation fluid sample is represented by block 520. The magnetic field pulse sequences used in the invention include an initial magnetic field pulse, a first portion and a second portion. Magnetic resonance signals from the sample are detected using the second portion of the magnetic field pulse sequence in block 522 and stored. In some embodiments, all magnetic resonance signals from the sample may be detected and stored. In other embodiments, magnetic resonance signals preceding a time $t_d$ after the initial pulse of the sequence may not be detected, or signals corresponding to time less than $t_d$ may be detected but not stored, or stored and later discarded, or stored and processed in a separate analysis.

The methods of the invention involve at least two magnetic field pulse sequences with differing first portions. A parameter J may be used (set, perhaps, at block 515) to indicate a total number of magnetic field pulse sequences to be generated. Decision block 525 represents querying whether $j=J$. If no, then j is incremented, as represented in block 526, and sequence parameters, such as $t_{long,j}$, or $\delta_j$ and $\Delta_j$, or $t_d$, are varied to modify the first portion of the sequence as represented in block 527, before the routine is returned to block 520 where the next sequence is generated in the sample. If $j=J$ when queried at decision block 525, then the data acquisition for the measurement is complete and the routine continues on to block 530 where j is re-initialized to $j=1$.

In some embodiments of the invention, two or more sequence parameters, for example, $\delta_j$ and $t_{d,j}$ or $t_{long,j}$ and $t_{d,i}$, are varied sequentially, such that, for each time $t_{d,i}$, a plurality of magnetic field pulse sequences are generated in the sample using a set of different time spacings, such as, $\delta_j$ or $t_{long,j}$. Then, time $t_{d,i}$ would be incremented, and a second plurality of magnetic field pulse sequences using the same set of time spacings is generated in the sample. To implement such embodiments would require initializing an additional parameter, $i=1$ (perhaps at block 515), and introducing an additional loop into the routine shown in FIG. 12 around, for example, blocks 515 and 530. After all the pluralities of magnetic field pulse sequences have been generated and magnetic resonance signals detected and stored, the parameter, i, would be re-initialized to $i=1$ before the routine proceeds.

Blocks 535 and 540 represent, respectively, analyzing the stored magnetic resonance signals starting at time $t_d$ and determining a relative amplitude of the $j^{th}$ sequence signal. The relative amplitude of the signal may be quantified as an attenuation factor, or the entire data set may be stored for later analysis. Block 545 represents querying whether all J sequences have been analyzed. If no, parameter j is incremented as indicated by block 546 and blocks 535 and 540 repeated until $j=J$. For embodiments of the invention involving an additional set of parameters, such as times, $t_{d,i}$, an additional loop would be introduced into the routine around, for example, block 535, or around blocks 535 and 545, to analyze the stored signals with respect to that parameter.

When all the relative amplitude data have been calculated, the amplitude data is used to extract information about the formation fluid, as represented by block 550. As discussed above, extracting information such as diffusion coefficient, saturation, fluid composition, etc. may involve calculating an attenuation factor; or fitting the amplitude data to an equation such as Equation 6, 7, or 8 and extracting information from the fit; or extracting a full two-dimensional function (such as to create a 3-D plot) and identifying different components and other information from the function or map; or combinations of such analyses.

The invention has been described herein with reference to certain examples and embodiments. It will, however, be evident that various modifications and changes may be made to the embodiments described above without departing from the scope of the invention as claimed.

We claim:

1. A method of extracting information about a fluid comprising:
   a) obtaining a fluid sample;
   b) generating a sequence of magnetic field pulses in the fluid, the sequence comprising an initial magnetic field pulse, a first portion that follows the initial magnetic field pulse, and a second portion that follows the first portion;
   c) detecting magnetic resonance signals using the second portion of the sequence;
   d) modifying the first portion of the sequence, and repeating steps (b) and (c); and
   e) extracting information about the fluid by determining relaxation and diffusion characteristics and their correlation based on the signals detected in steps (c) and (d).

2. The method of claim 1, wherein the second portion comprises a series of magnetic field pulses separated by a time spacing.

3. The method of claim 2, wherein the first portion comprises a first series of magnetic field pulses separated by a first time spacing.

4. The method of claim 3, wherein the first time spacing is not less than the time spacing of the second portion.

5. The method of claim 2, wherein the first portion comprises a stimulated echo sequence.

6. The method of claim 1, wherein the first portion includes at least one magnetic field gradient pulse.

7. The method of claim 1, wherein modifying the first portion comprises varying a time spacing between magnetic field pulses.

8. The method of claim 1, wherein analyzing magnetic resonance signals comprises calculating an attenuation factor.

9. The method of claim 1, wherein analyzing magnetic resonance signals comprises determining a relative amplitude of the magnetic resonance signals.

10. The method of claim 1, wherein extracting information about the fluid comprises determining a diffusion coefficient.

11. The method of claim 1, wherein extracting information about the fluid comprises distinguishing between different components of the fluid.

12. The method of claim 1, wherein the fluid is a formation fluid.

13. The method of claim 1, further comprising:
   f) repeating step (d) a plurality of times.

14. The method of claim 13, wherein extracting information about the fluid comprises extracting a two dimensional function of a first parameter indicative of the fluid versus a second parameter indicative of the fluid.

15. The method of claim 14, wherein the first parameter is a diffusion coefficient.

16. The method of claim 14, wherein a second parameter is a relaxation time.

17. The method of claim 13, further comprising:
   g) varying the time relative to the initial magnetic field pulse from which the magnetic resonance signals are analyzed and repeating steps (b) through (f).

18. The method of claim 17, further comprising repeating step (g) a plurality of times.

19. The method of claim 17, wherein extracting information about the fluid comprises determining a time dependent diffusion coefficient.

20. A method of extracting information about a fluid comprising:
   a) obtaining a fluid sample;
   b) generating a first sequence of magnetic field pulses in the fluid, the first sequence comprising a first portion and a second portion;
   c) detecting magnetic resonance signals using the second portion of the first sequence;
   d) generating at least one other sequence of magnetic field pulses in the fluid, each other sequence comprising a third portion and a fourth portion, the third portion having a different sensitivity to diffusion effects than the first portion of the first sequence and the fourth portion having a similar sensitivity to diffusion effects as the second portion of the first sequence;
   e) detecting magnetic resonance signals using the fourth portion of each other sequence; and
   f) analyzing the detected magnetic resonance signals to separate diffusion effects from relaxation effects.

21. The method of claim 20, wherein the first portion of the first sequence is substantially similar to the second portion of the first sequence.

22. The method of claim 21, wherein the first sequence of magnetic field pulses is generated according to:

$$90-[t_{short}-180-t_{short}-echo_i]_n$$

wherein $t_{short}$ is a time spacing; $echo_i$ is the $i^{th}$ magnetic resonance spin echo; and n is the number of spin echoes.

23. The method of claim 20, wherein the first sequence comprises a modified CPMG sequence.

24. The method of claim 23, wherein the first sequence is generated according to:

$$90-[t_{long}-180-t_{long}-echo_k]_m-[t_{short}-180-t_{short}-echo_{i'}]_{n'}$$

wherein $t_{long}$ is a first time spacing; $echo_k$ is the $k^{th}$ magnetic resonance spin echo of the first portion; m is the number of spin echoes of the first portion; $t_{short}$ is a second time spacing, the second time spacing being shorter than the first time spacing; $echo_{i'}$ is the $i'^{th}$ magnetic resonance spin echo of the second portion; and n' is the number of spin echoes of the second portion.

25. The method of claim 23, wherein the first sequence is generated according to:

$$90-[\delta-90-(\Delta-\delta)-90-\delta-echo_k]_m-[t_{short}-180-t_{short}-echo_i]_{n'}$$

wherein $\delta$ and $\Delta$ are time spacings in the first portion; $echo_k$ is the $k^{th}$ stimulated magnetic resonance spin echo of the first portion; m is the number of stimulated spin echoes of the first portion; $t_{short}$ is a time spacing in the second portion; $echo_i$ is the $i^{th}$ magnetic resonance spin echo of the second portion; and n' is the number of spin echoes of the second portion.

26. The method of claim 20, wherein the other sequence comprises a modified CPMG sequence.

27. The method of claim 26, wherein at least one other sequence is generated according to:

$$90-[t_{long,j}-180-t_{long,j}-echo_{k,j}]_{m,j}-[t_{short}-180-t_{short}-echo_{i',j}]_{n',j}$$

wherein, for the $j^{th}$ other sequence, $t_{long,j}$ is a third time spacing; $echo_{k,j}$ is the $k^{th}$ magnetic resonance spin echo of the third portion; (m,j) is the number of spin echoes of the third portion; $t_{short}$ is a fourth time spacing, the fourth time spacing being shorter than the third time spacing; $echo_{i',j}$ is the $i'^{th}$ magnetic resonance spin echo of the fourth portion; and (n',j) is the number of spin echoes of the fourth portion.

28. The method of claim 26, wherein at least one other sequence is generated according to:

$$90\text{-}[\delta_j\text{-}90\text{-}(\Delta_j\text{-}\delta_j)\text{-}90\text{-}\delta_j\text{-}echo_{kj}]_{mj}\text{-}[t_{short}\text{-}180\text{-}_{short}\text{-}echo_{i'j}]_{n'j}$$

wherein, for the $j^{th}$ other sequence, $\delta_j$ and $\Delta_j$ are time spacings in the third portion; $echo_{k,j}$ is the $k^{th}$ stimulated magnetic resonance spin echo of the third portion; (m,j) is the number of stimulated spin echoes of the third portion; $t_{short}$ is a time spacing in the fourth portion; $echo_{i'j}$ is the $i'^{th}$ magnetic resonance spin echo of the fourth portion; and (n',j) is the number of spin echoes of the fourth portion.

29. The method of claim 20, wherein the first portion and the third portion include at least one magnetic field gradient pulse.

30. The method of claim 20, wherein analyzing magnetic resonance signals comprises determining an amplitude of the signal from the other sequence relative to an amplitude of the signal from the first sequence.

31. The method of claim 20, wherein analyzing magnetic resonance signals comprises analyzing spin echoes from the first sequence that correspond in time to spin echoes from the other sequence.

32. The method of claim 20, wherein analyzing magnetic resonance signals comprises analyzing a substantially equal number of spin echoes from the first sequence and from the other sequence.

33. The method of claim 20, further comprising extracting a two-dimensional function of two parameters indicative of the fluid.

34. The method of claim 20, wherein the fluid is a formation fluid.

35. The method of claim 20, wherein analyzing magnetic resonance signals comprises correlating spin echoes from the first sequence in time with spin echoes from the other sequence and analyzing correlated spin echoes at a given time, and further comprising:

g) varying the given time at which correlated spin echoes are analyzed, and h) repeating steps (b) through (g) a plurality of times.

36. The method of claim 35, further comprising determining a time dependent attribute of the fluid.

37. A method of extracting information about a fluid comprising:

a) obtaining a fluid sample;

b) generating a fist sequence of magnetic field pulses in the fluid, the first sequence comprising a first series of magnetic field pulses with a first time spacing;

c) detecting spin echoes using the first series;

d) generating a second sequence of magnetic field pulses in the fluid, the second sequence comprising a second series of magnetic field pulses with a second time spacing and a third series of magnetic field pulses with the first time spacing, the second spacing being greater than the first time spacing;

e) detecting spin echoes using the third series;

f) developing a correlation between diffusion and relaxation time using said detected spin echoes and;

g) extracting information about the fluid using spin echoes detected using the first series and spin echoes detected using the third series.

38. The method of claim 37, wherein extracting information comprises analyzing spin echoes detected using the first series that correspond in time to spin echoes detected using the third series.

39. The method of claim 37, wherein extracting information comprises analyzing a substantially equal number of spin echoes detected using the first series and the third series.

40. The method of claim 37, wherein extracting information comprises determining an amplitude of the spin echoes detected using the third series relative to an amplitude of the spin echoes detected using the first series.

41. The method of claim 37, further comprising:

g) generating at least one other sequence of magnetic field pulses in the fluid, each other sequence comprising a fourth series of magnetic field pulses with a time spacing greater than the first time spacing and different from the second time spacing and from each other, and a fifth series of magnetic field pulses with the first time spacing; and h) detecting spin echoes using the fifth series, wherein information about the fluid is extracted using the spin echoes detected using the first series, the third series, and the fifth series.

42. The method of claim 41, wherein extracting information comprises analyzing spill echoes detected using the first series that correspond in time to spin echoes detected using the fifth series.

43. The method of claim 41, wherein extracting information comprises analyzing a substantially equal number of spin echoes detected using the first series and the fifth series.

44. The method of claim 41, wherein extracting information comprises extracting a two-dimensional function of a first parameter and a second parameter indicative of the fluid.

45. The method of claim 44, wherein the first parameter is a diffusion coefficient and the second parameter is a relaxation time.

46. A logging apparatus comprising: a logging tool that is moveable through a borehole, wherein said logging tool is equipped with a fluid sampling means; and a processor that is coupled with the logging tool, the processor being programmed with instructions which, when executed by the processor cause the logging tool to:

i) generate a sequence of magnetic field pulses in a fluid sample, the sequence comprising an initial magnetic field pulse, a first portion, and a second portion;

ii) detect magnetic resonance signals produced from the fluid sample using the second portion of the sequence;

iii) modify the first portion of the sequence and repeat steps (i) and (ii); and cause the processor to:

iv) analyze magnetic resonance signals from a time relative to the initial magnetic field pulse and extract information about the fluid sample, including the correlation between diffusion and relaxation.

47. The logging apparatus of claim 46, wherein the second portion comprises a series of magnetic field pulses separated by a time spacing.

48. The logging apparatus of claim 46, wherein the first portion comprises a first series of magnetic field pulses separated by a first time spacing.

49. The logging apparatus of claim 46, wherein the first portion comprises a stimulated echo sequence.

50. The logging apparatus of claim 46, wherein the instructions, when executed by the processor, cause the logging tool to:

v) repeat step iii) a plurality of times.

51. The logging apparatus of claim 50, wherein the instructions, when executed by the processor, cause the processor to extract a two-dimensional function of two parameters that characterize the fluid sample.

52. The logging apparatus of claim 50, wherein the instructions, when executed by the processor, cause the processor to vary the time relative to the initial magnetic field pulse from which the magnetic resonance signals are analyzed and repeat steps i) through v).

53. A logging apparatus comprising:
   a logging tool that is moveable through a borehole, wherein said logging tool is equipped with a fluid sampling means; and
   a processor that is coupled with the logging tool, the processor being programmed with instructions which, when executed by the processor:
      cause the logging tool to:
         i) generate a first sequence of magnetic field pulses in a fluid sample, the first sequence comprising a first portion and a second portion;
         ii) detect magnetic resonance spin echoes produced from the fluid sample using the second portion of the first sequence;
         iii) generate at least one other sequence of magnetic field pulses in the fluid sample, each other sequence comprising a third portion and a fourth portion, the third portion having a different sensitivity to diffusion effects than the first portion of the first sequence and the fourth portion having a similar sensitivity to diffusion effects as the second portion of the first sequence;
         iv) detect magnetic resonance spin echoes produced from the fluid sample using the fourth portion of each other sequence; and
      cause the processor to:
         v) analyze detected spin echoes to separate diffusion effects from relaxation effects.

54. The logging apparatus of claim 53, wherein the first portion of the first sequence is substantially similar to the second portion of the first sequence.

55. The logging apparatus of claim 54, wherein the first sequence comprises a CPMG sequence.

56. The logging apparatus of claim 53, wherein the first sequence comprises a modified CPMG sequence.

57. The logging apparatus of claim 53, wherein the other sequence comprises a modified CPMG sequence.

58. The logging apparatus of claim 53, wherein the instructions, when executed by the processor, cause the processor to analyze a substantially equal number of spin echoes detected using the second portion of the first sequence and detected using the fourth portion of the other sequence.

59. The logging apparatus of claim 53, wherein the instructions, when executed by the processor, cause the processor to analyze spin echoes detected using the second portion that correspond in time to spin echoes detected using the fourth portion.

60. The logging apparatus of claim 53, wherein step v) involves analyzing spin echoes at a given time, and the instructions, when executed by the processor, cause the processor to vary the given time.

61. A logging apparatus comprising:
   means for sampling a formation fluid; means for generating a sequence of magnetic field pulses in a formation fluid sample, the sequence comprising an initial magnetic field pulse, a first portion and a second portion, means for detecting magnetic resonance signals using the second portion; means for modifying the first portion; and means for analyzing magnetic resonance signals from a time relative to the initial magnetic field pulse to extract information about the formation fluid including the correlation between diffusion and relaxation.

62. The logging apparatus of claim 61, further comprising means for generating magnetic field gradient pulses in the formation fluid sample.

63. A logging apparatus comprising:
   means for sample a formation fluid;
   means for generating a first sequence of magnetic field pulses in the formation fluid sample, the first sequence comprising a first portion and a second portion;
   means for detecting magnetic resonance signals from the formation fluid sample using the second portion of the first sequence;
   means for generating at least one other sequence of magnetic field pulses in the formation fluid sample, each other sequence comprising a third portion and a fourth portion, the third portion having a different sensitivity to diffusion effects than the first portion of the first sequence and the fourth portion having a similar sensitivity to diffusion effects as the second portion of the first sequence;
   means for detecting magnetic resonance signals from the formation fluid sample using the fourth portion of each other sequence; and
   means for analyzing magnetic resonance signals to separate diffusion effects from surface and bulk relaxation effects.

64. The logging apparatus of claim 63, further comprising means for generating magnetic field gradient pulses in the formation fluid sample.

* * * * *